(12) United States Patent
Zhu

(10) Patent No.: US 10,238,688 B2
(45) Date of Patent: Mar. 26, 2019

(54) COMBINATION THERAPIES FOR BLADDER CANCER

(71) Applicant: GENEDIA BIOTECH CO. LTD., Kunshan, Jiangsu (CN)

(72) Inventor: Jingde Zhu, Jiangsu (CN)

(73) Assignee: Genedia Biotech Co., Ltd., Kunshan, Jiangsu (CN)

( * ) Notice: Subject to any disclaimer, the term of this patent is extended or adjusted under 35 U.S.C. 154(b) by 0 days.

(21) Appl. No.: 15/552,922

(22) PCT Filed: Apr. 24, 2015

(86) PCT No.: PCT/CN2015/077346
§ 371 (c)(1),
(2) Date: Aug. 23, 2017

(87) PCT Pub. No.: WO2016/169042
PCT Pub. Date: Oct. 27, 2016

(65) Prior Publication Data
US 2018/0028563 A1 Feb. 1, 2018

(51) Int. Cl.
| | |
|---|---|
| *A61K 9/00* | (2006.01) |
| *A61K 9/20* | (2006.01) |
| *A61K 31/24* | (2006.01) |
| *A61K 33/24* | (2006.01) |
| *A61K 31/407* | (2006.01) |
| *A61K 31/704* | (2006.01) |

(52) U.S. Cl.
CPC ............ *A61K 33/24* (2013.01); *A61K 9/0053* (2013.01); *A61K 9/20* (2013.01); *A61K 31/24* (2013.01); *A61K 31/407* (2013.01); *A61K 31/704* (2013.01)

(58) Field of Classification Search
USPC .......................................................... 514/649
See application file for complete search history.

(56) References Cited

U.S. PATENT DOCUMENTS 6,458,389 B1 * 10/2002 Debregeas ............ A61K 9/1676
424/489
2014/0296173 A1 * 10/2014 Borbely ................ A61K 31/704
514/34

FOREIGN PATENT DOCUMENTS

WO WO 2014/151853 9/2014

OTHER PUBLICATIONS

Epirubin Product Specification, Teva Pharmaceutical Australia 2009 in view of WC et al, Urology. Apr. 1986; 27(4):335-9.*
WC et al, Urology. Apr. 1986; 27(4):335-9.*
Hsin et al, Urologic Oncology: Seminars and Original Investigations 30 (2012) 421-427.*
International Search Report and Written Opinion for PCT/CN2015/077346 filed Apr. 24, 2015 dated Jan. 25, 2016 (8 pages).

* cited by examiner

*Primary Examiner* — Jean P Cornet
(74) *Attorney, Agent, or Firm* — Sheppard Mullin Richter & Hampton LLP

(57) ABSTRACT

The disclosure provides drug combinations and methods for treating human bladder cancer. The drug combination may include mitomycin, or an analog thereof, cisplatin or an alternative platinum drug, and epirubicin or an alternative anthracycline drug and does not include gemcitabine.

13 Claims, 9 Drawing Sheets

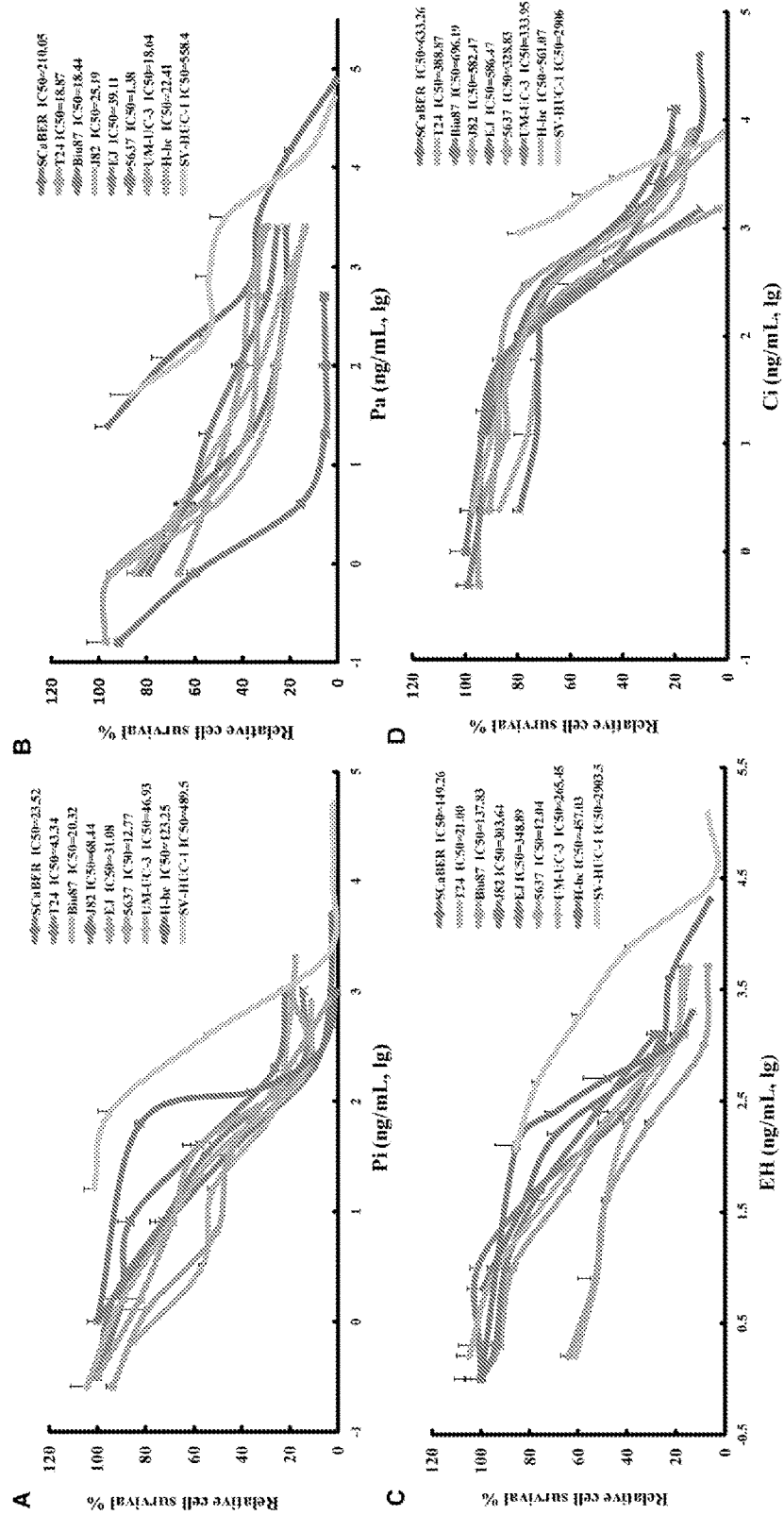
FIG. 2A-D

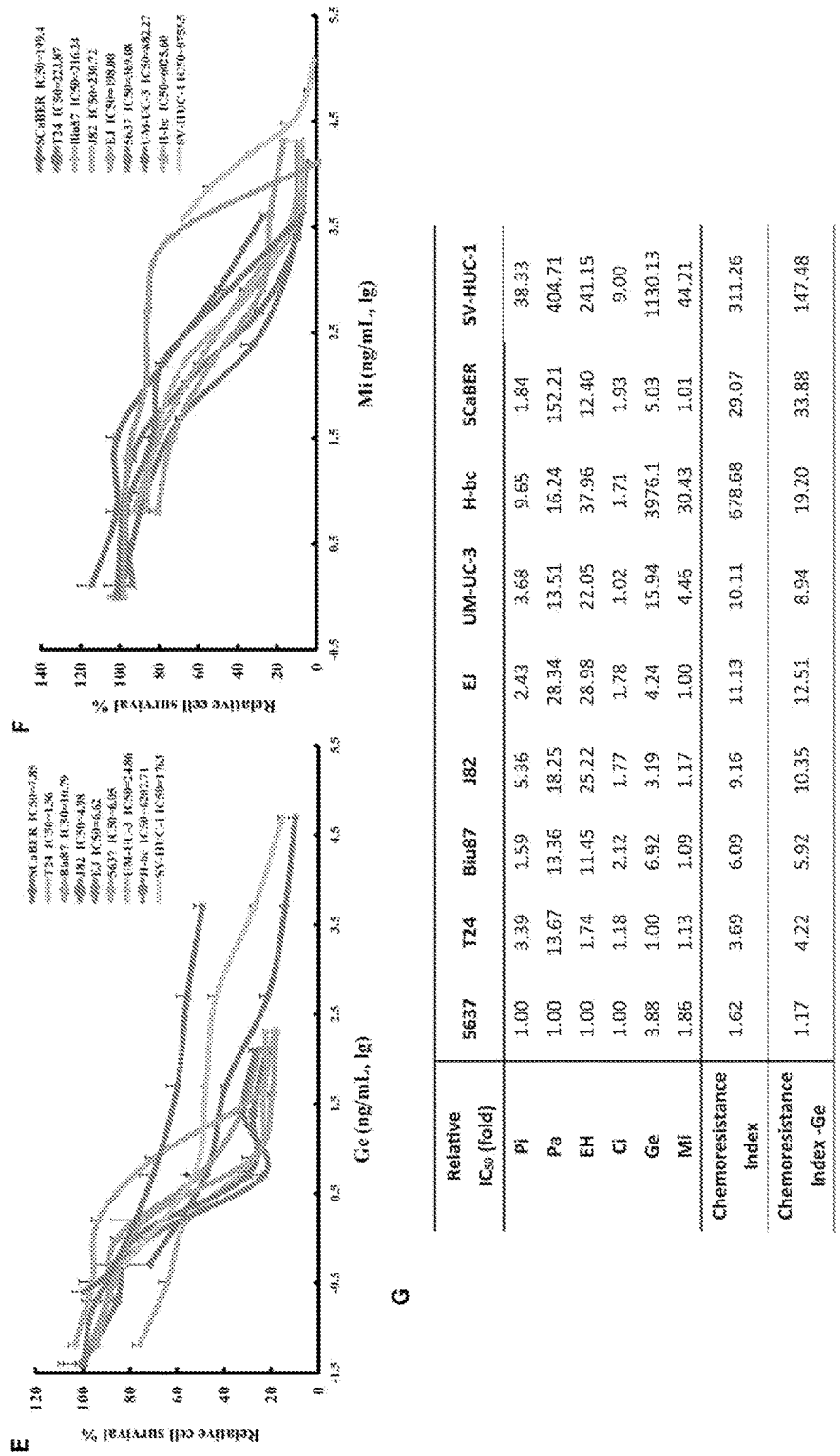
FIG. 2E-G

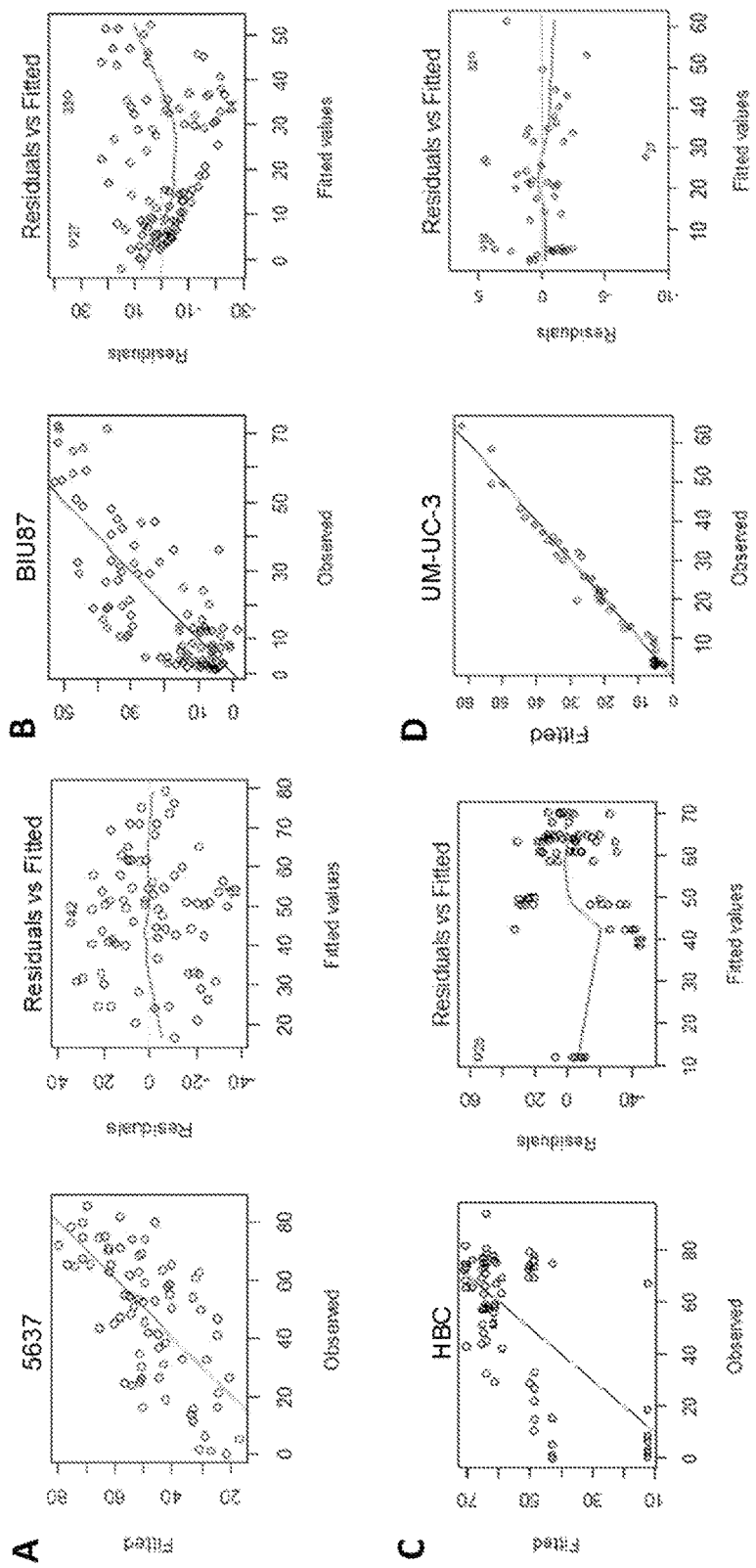
FIG. 3A-D

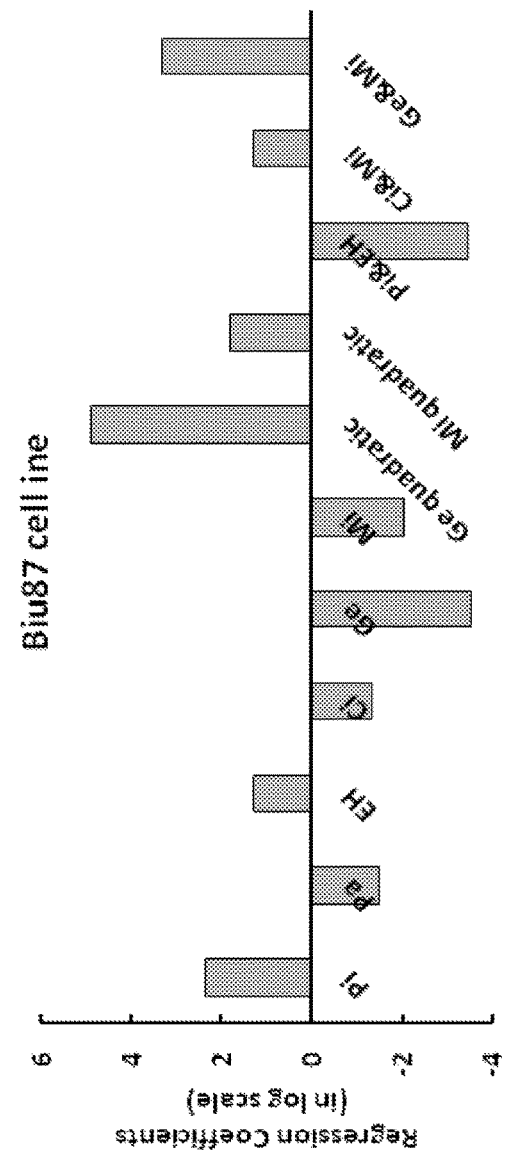
FIG. 3E-F

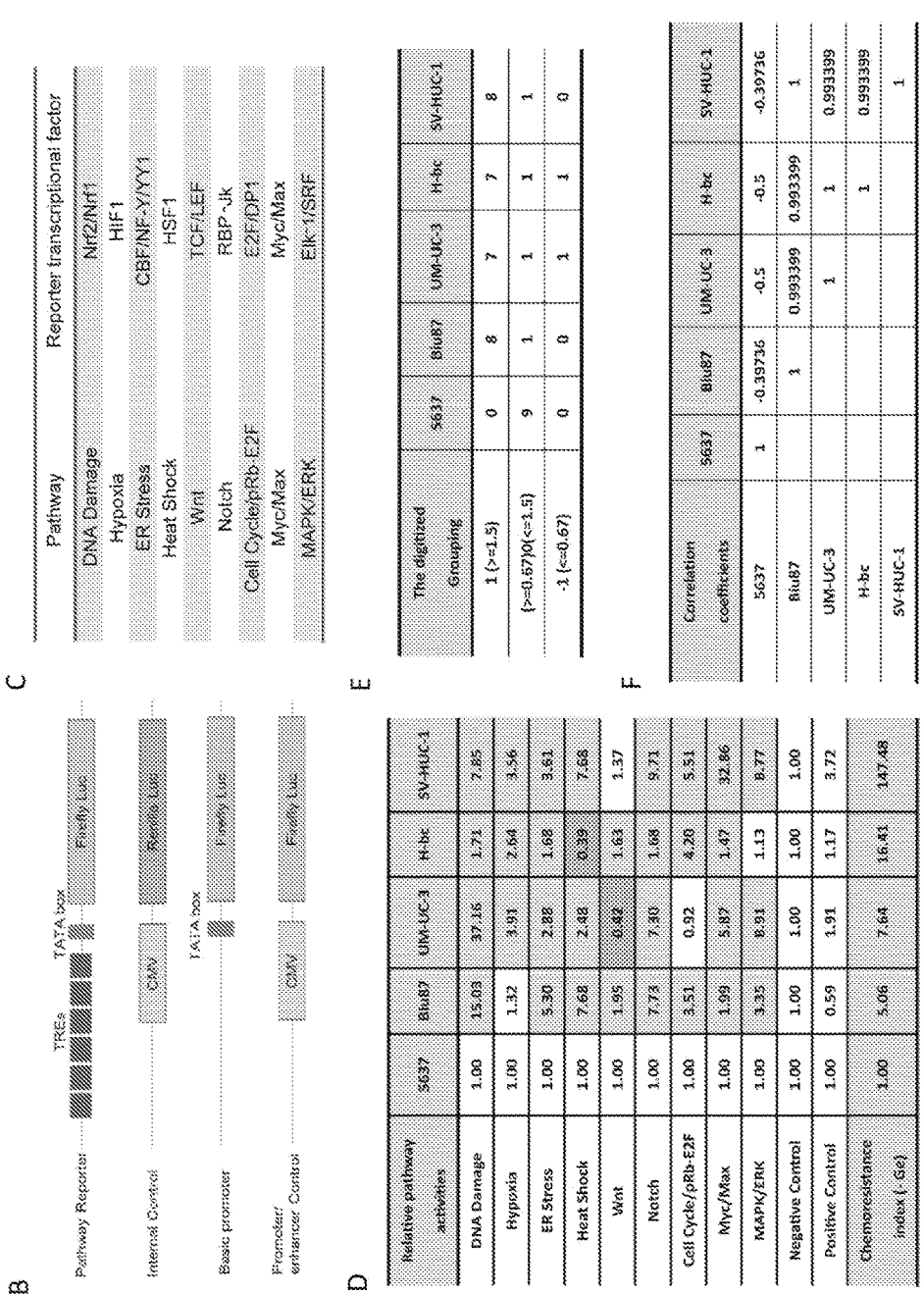
FIG. 4B-F

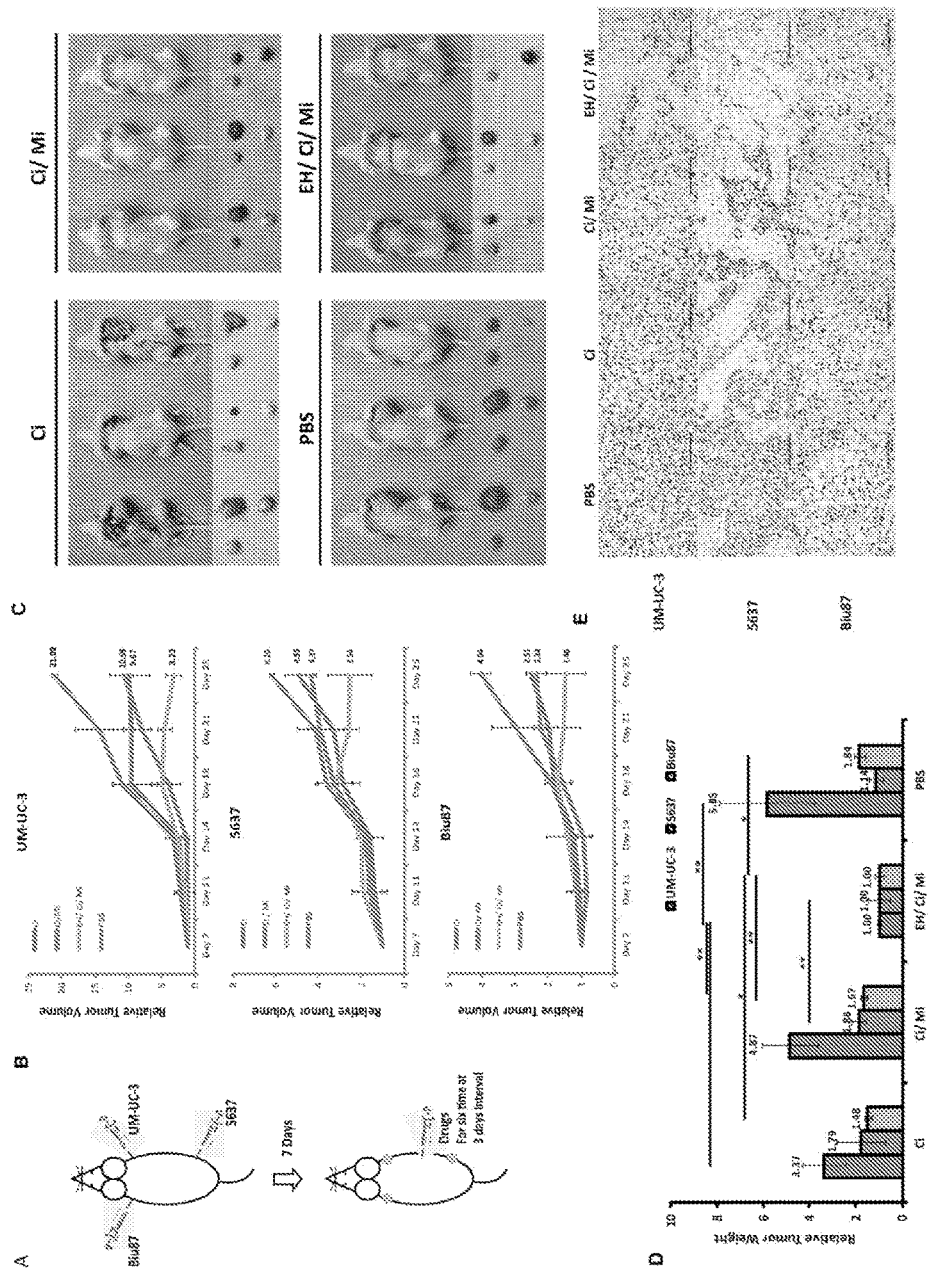
FIG. 5A-E

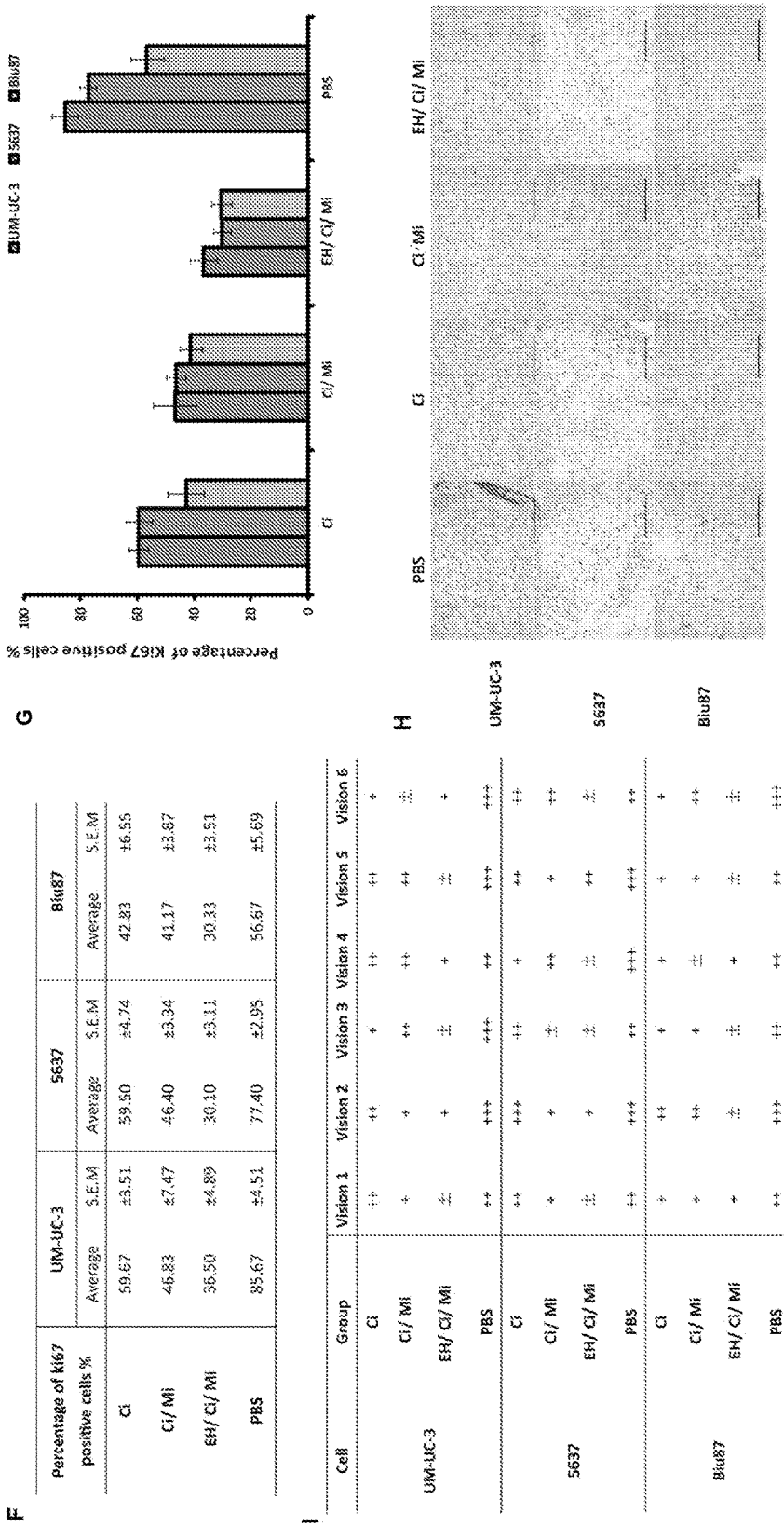
FIG. 5F-H

COMBINATION THERAPIES FOR BLADDER CANCER

CROSS-REFERENCE TO RELATED APPLICATIONS

This application is a U.S. National Stage Application under 35 U.S.C. § 371 of International Application No. PCT/CN2015/077346, filed Apr. 24, 2015, the entirety of each of which is incorporated herein by reference.

BACKGROUND OF THE DISCLOSURE

Bladder cancer is the fourth most common neoplasm worldwide in males with notoriously high recurrence and chemo-therapy refractoriness. Transitional cell carcinoma (TCC) accounts for more than 90% and squamous cell carcinoma for about 6% to 8% of bladder tumors. Bladder cancer is often heterogeneous. That is, there are more than one sub-types of bladder cancer cells in a bladder cancer patient.

In chemotherapy, the response rates are fairly low, usually between 5%-55%. The low success rate is at least in part because of cancer heterogeneity. A therapy that is suitable for one sub-type of cancer cells may not be efficacious for another. Combination chemotherapies that simultaneously target several mechanisms in cancer cells, in particular those involved in cancer cell survival, are expected to have better therapeutic index than mono-drug regimens. This has shown success for fairly homogenous cancers but it is not clear whether combination therapies have similar advantage for heterogeneous cancers like bladder cancer.

Searching for a potential optimal combination from a large pool of drugs is a prohibitive task, and more so for a cancer such as bladder cancer with high heterogeneity. Therefore, there is a need for improved methods for efficiently identifying potentially useful drug combinations for treating bladder cancer as well as the resulting combinations.

SUMMARY

The disclosure provides, in one embodiment, a method for treating a human patient suffering from bladder cancer. In one aspect, the method entails administering to the patient an effective amount of mitomycin, or an analogue thereof, and an effective amount of a platinum drug (e.g., cisplatin, carboplatin, oxaliplatin, satraplatin, picoplatin, nedaplatin, triplatin, and lipoplatin). In one embodiment, the method further includes administering to the patient an effective amount of an anthracycline drug (e.g., epirubicin, pirarubicin, doxorubicin, daunorubicin, idarubicin, valrubicin, and mitoxantrone).

Also provided, in one embodiment, is a method for treating a human patient suffering from bladder cancer, comprising administering to the patient an effective amount of mitomycin and an effective amount of cisplatin, carboplatin or oxaliplatin. In one embodiment, the method further comprises administering to the patient an effective amount of epirubicin, pirarubicin or doxorubicin. In one embodiment, the method further comprises administering to the patient an effective amount of epirubicin.

In some aspects, the patient is not being treated with gemcitabine. In some aspects, the patient is not being treated with paclitaxel or docetaxel. In some aspects, the patient is not being treated with fluorouracil (5-FU), methotrexate or vinblastine. In some aspects, the patient is not being treated with any other chemotherapeutic drugs. In some aspects, the patient is not being treated with any other drug that is not an analogue of mitomycin, a platinum drug, or an anthracycline drug.

In some aspects, the method does not include administering to the patient gemcitabine. In some aspects, the method does not include administering to the patient paclitaxel or docetaxel. In some aspects, the method does not include administering to the patient fluorouracil (5-FU), methotrexate or vinblastine. In some aspects, the method does not include administering to the patient any other chemotherapeutic drugs. In some aspects, the method does not include administering to the patient any other drug that is not an analogue of mitomycin, a platinum drug, or an anthracycline drug.

In some aspects, the mitomycin is administered intravesically. In one aspect, the amount of mitomycin administered is from 20 mg to 60 mg in each treatment.

In some aspects, the cisplatin, carboplatin or oxaliplatin is administered intravesically. In one aspect, the amount of cisplatin, carboplatin or oxaliplatin administered is from 50 mg to 150 mg in each treatment.

In some aspects, the epirubicin is administered intravesically. In one aspect, the amount of epirubicin administered is from 5 mg to 200 mg in each treatment.

In some aspects, (a) the mitomycin, (b) the cisplatin, carboplatin or oxaliplatin, and (c) the epirubicin, pirarubicin or doxorubicin are administered orally.

In some aspects, the mitomycin and the cisplatin, carboplatin or oxaliplatin are administered concurrently. In some aspects, the mitomycin and the cisplatin, carboplatin or oxaliplatin are administered sequentially.

In some aspects, the bladder cancer comprises transitional cell carcinoma. In some aspects, the patient is further treated with radiation therapy.

Another embodiment of the disclosure provides a method for treating a human patient suffering from bladder cancer, comprising administering to the patient an effective amount of mitomycin, an effective amount of cisplatin, and an effective amount of epirubicin. In some aspects, the patient is not being treated with any of gemcitabine, paclitaxel, docetaxel, fluorouracil (5-FU), methotrexate or vinblastine.

In one aspect, the mitomycin, cisplatin, and epirubicin are administered intravesically.

Also provided, in one embodiment, is a composition comprising mitomycin, cisplatin and epirubicin. Also provided, in one embodiment, is a composition consisting essentially of mitomycin, cisplatin and epirubicin and does not include another chemotherapeutic agent. Also provided, in one embodiment, is a composition the composition is a tablet or a solution.

Likewise, provided in one embodiment is a kit or package comprising, in separate compartments, mitomycin, cisplatin and epirubicin. Also provided, in one embodiment, is a kit consisting essentially of mitomycin, cisplatin and epirubicin and does not include another chemotherapeutic agent.

BRIEF DESCRIPTION OF THE DRAWINGS

FIG. 2A-G show the chemoresistance profile of bladder cancer and immortalized untransformed cell lines. The relative cell survival (%) of the drug treated over the no drug treated cells (Y-axis) was plotted against the dose (ng/mL, lg) of the following six drugs (X-axis): Pi, Pa, EH, Ge, Ci and Mi, respectively, and plotted, (panel A-F) the curves are indicated for SCaBER, T24, Biu87, J82, EJ, 5637, UM-UC-3, H-bc and SV-HUC-1 cell lines, respectively. (G) The relative $IC_{50}$ (fold) of each drug with the lowest $IC_{50}$ (ng/mL, lg) as reference is calculated and shown in table.

FIG. 3A-F present the results of statistic modeling analysis. Both experimental data from the DE algorithm guided testing and the model-predicted results of (A) 5637 (B) Biu87 (C) H-bc and (D) UM-UC-3 cell lines are plotted together for comparison. (E) The Linear regression model analysis of the results in Biu8 cell line indicates that Ge was not a favored drug for combination and should not be further used. (F) The summary of the combination ability of each pair drugs from the statistic modeling analysis.

FIG. 4A-F show the activity of nine pathways in five cell lines of distinct chemoresistance. (A) The scheme of pathway analysis. (B) The firefly luciferase reporter constructs used for the pathway analyses. 1) "Basic promoter" reporter (the negative control in D), 2) "Pathway reporter", where the tandem repeat of the DNA motif bound by the master transcription factor in each pathway is inserted at upstream of the firefly luciferase gene in "Basic promoter" reporter, 3) "Internal control", the *Renilla* lucfierase gene is under the control of both CMV viral promoter and enhancer (to control for transfection efficacy), and 4) "Promoter/enhancer control", the firefly luciferase gene is under the control of both CMV viral promoter and enhancer (the positive control in D). (C) The nine pathways and each's master transcription factor. (D) The normalized activity of each pathways versus the negative control in 5637 is set at 1 (original data in Table S5). The normalized pathway activity of all five cell lines is normalized to that in 5637 (fold) in the Table. The pathways with its activity higher by 0.5 fold or more are marked in yellow and lower by 0.5 fold in green. (E) The relative pathway activities are digitalized and sorted in each of the following three groups: (1), activated: the pathways with the activities elevated by no less than 0.5 fold by drug; (−1), inactivated: the pathways with the activities down by no less than 0.5 fold by drug and (0), no responding: none of the above two cases. (F) The correlation coefficients of each pair of the indicated cell lines.

FIG. 5A-H show the effects of the EH/Ci/Mi regimen on in vivo tumor growth in a xenograft/nude mice model. (A) The experimental scheme. (B) Relative growth profile of UM-UC-3, 5637 and Biu87 tumor xenografts in nude mice. Y-axis: The mean and +−SD of the relative tumor volume (3 mice per group) measured on the indicated day over the volume on day 7th. (C) The tumors and nude mice on day 28th when the experiment was terminated. (D) Tumor weights on the $28^{th}$ day. The mean and +−SD of the relative tumor weight (3 mice per group) over that the EH/Ci/Mi was plotted *: p<0.05; **: p<0.02. (E) The representative Ki67 images of tumor xenografts subjected to immunological staining with Ki67 antibody. Photographs were taken under a microscope at 200× magnification, scale bar units: 100 μm. (F) Summary of Ki67 positive cell counts (2 slides per tumor×3 tumors in each group). Data were expressed as the mean±S.E.M. and plotted (G). (H) Representative CD34 immuno-staining images. Photographs were taken under a microscope at 200× magnification. (I) Summary of CD34 positive cells for each group (2 slides per tumor×3 tumors in each group). Immunohistochemistry staining level of CD34 positive vasculature were described as: ±, no staining; +, weak staining; ++, moderate staining; and +++, strong staining.

DETAILED DESCRIPTION OF THE DISCLOSURE

Figure 1:
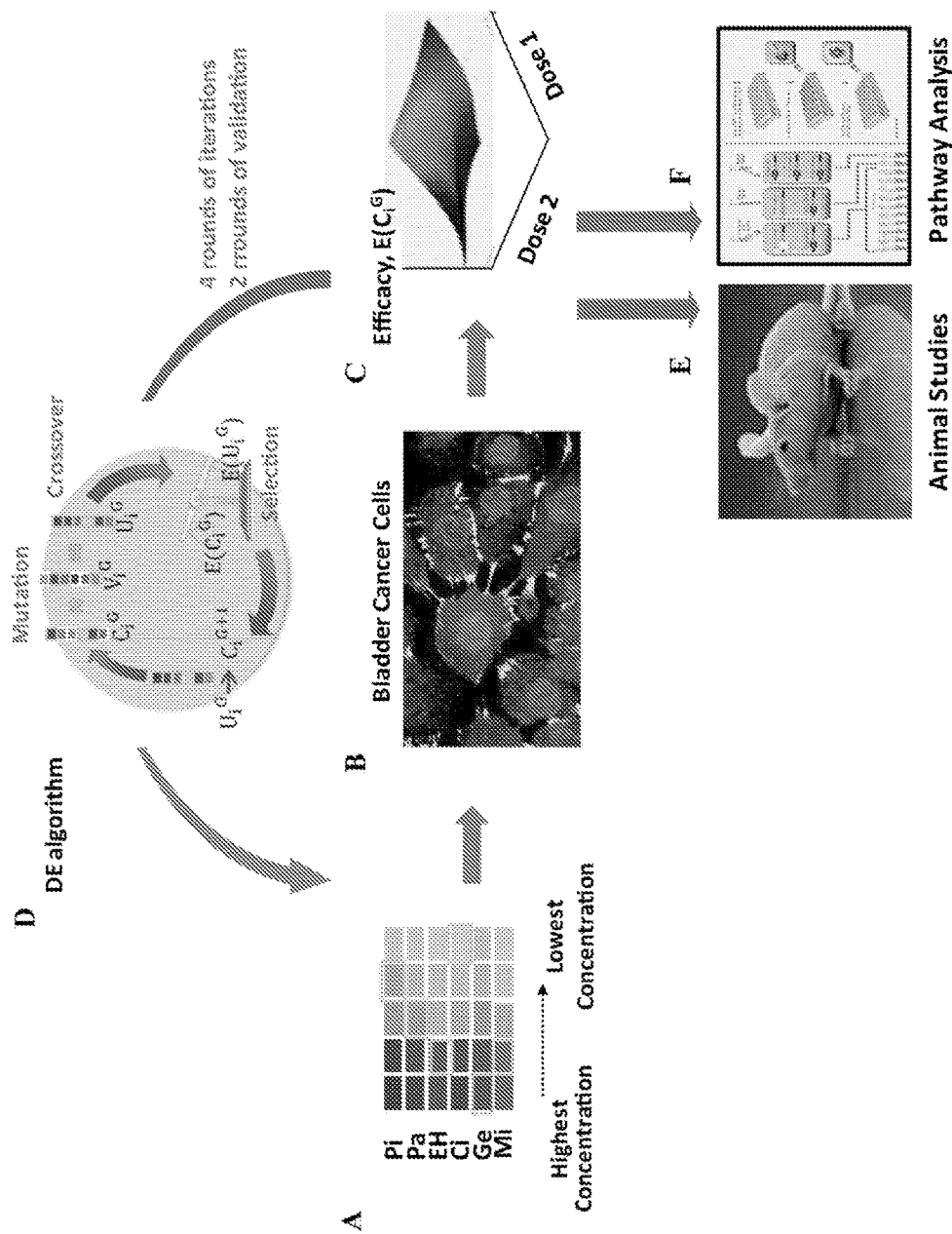
FIG. 1A-F show a scheme of the study in Example 1. (A) The drug-dose pool suggested from the chemoresistance profiling, consists of six drugs at five doses. The multi-drug combinations are generated by "Differential Evolution" (DE) algorithm from a matrix of six different drugs at five different doses. (B) The cells are subjected to treatment with the multi-drug combinations. The accumulated cell survival (ACS) is derived from the combined cell survival (%) of each cell line under the drug treatment. g combinations in each round of testing (iteration) were fed into the FSC scheme to generate the combinations for the subsequent round of iterations. (C) Measuring of the efficacy of the combinations. (D) Guided by the differential evolution algorithm deriving new drug-dose combination. Repeat B, C and D, until the optimal drug-dose combination has reached. The statistical modeling of the experimental data generated by 4 rounds of iterations, validation (2 rounds). (E) The tumor inhibition efficacy of EH/Ci/Mi was compared with its bi- and mono-drug counterparts in the three-cell line-derived tumor xenograft/nude mice systems. (F) Pathway analysis, the activity of sixteen chemo-resistance associated pathways was determined under base line or drug treated EH/Ci/Mi regimen or the single drug at four fold dose in the following four bladder cancer cell lines: 5637, Biu87, UM-UC-3 and H-bc and the normal cell line: SV-HUC-1.

Throughout this disclosure, various publications, patents and published patent specifications are referenced by an identifying citation. The disclosures of these publications, patents and published patent specifications are hereby incorporated by reference into the present disclosure to more fully describe the state of the art to which this disclosure pertains.

Definitions

As used herein, certain terms may have the following defined meanings. As used in the specification and claims, the singular form "a," "an" and "the" include singular and plural references unless the context clearly dictates otherwise. For example, the term "a cell" includes a single cell as well as a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

As used herein, the term "patient" intends an animal, a mammal or yet further a human patient. For the purpose of illustration only, a mammal includes but is not limited to a human, a simian, a murine, a bovine, an equine, a porcine or an ovine.

The term "treating" as used herein is intended to encompass curing as well as ameliorating at least one symptom of the condition or disease. For example, in the case of cancer, a response to treatment includes a reduction in cachexia, increase in survival time, elongation in time to tumor progression, reduction in tumor mass, reduction in tumor burden and/or a prolongation in time to tumor metastasis, time to tumor recurrence, tumor response, complete response, partial response, stable disease, progressive disease, progression free survival, overall survival, each as measured by standards set by the National Cancer Institute and the U.S. Food and Drug Administration for the approval of new drugs. See Johnson et al. (2003) J. Clin. Oncol. 21(7):1404-1411.

"An effective amount" intends to indicate the amount of a compound or agent administered or delivered to the patient which is most likely to result in the desired response to treatment. The amount is empirically determined by the patient's clinical parameters including, but not limited to the stage of disease, age, gender, histology, sensitivity, toxicity and likelihood for tumor recurrence.

The term "clinical outcome", "clinical parameter", "clinical response", or "clinical endpoint" refers to any clinical observation or measurement relating to a patient's reaction to a therapy. Non-limiting examples of clinical outcomes include tumor response (TR), overall survival (OS), progression free survival (PFS), disease free survival (DFS), time to tumor recurrence (TTR), time to tumor progression (TTP), relative risk (RR), toxicity or side effect.

As used herein, the terms "Stage I cancer," "Stage II cancer," "Stage III cancer," and "Stage IV" refer to the TNM staging classification for cancer. Stage I cancer typically identifies that the primary tumor is limited to the organ of origin. Stage II intends that the primary tumor has spread into surrounding tissue and lymph nodes immediately draining the area of the tumor. Stage III intends that the primary tumor is large, with fixation to deeper structures. Stage IV intends that the primary tumor is large, with fixation to deeper structures. See pages 20 and 21, CANCER BIOLOGY, $2^{nd}$ Ed., Oxford University Press (1987).

Descriptive Embodiments

The disclosure, in one embodiment, further provides compositions and methods for treating cancer, in particular bladder cancer.

Even though it has been suggested that combination chemotherapies offer great promises in cancer treatment, little success has been made and the search for promising combinations remains challenging. The present disclosure demonstrates a heuristic method that efficiently searches for promising drug combinations from six chemotherapeutic drugs through testing with 10 cell lines with different chemoresistance profiles. The drugs included Pirarubicin (Pi), Paclitaxel (Pa), Epirubicin Hydrochloride (EH), Cisplatin (Ci), Gemcitabine (Ge) and Mitomycin (Mi), and the cell lines included eight human bladder cancer cell lines (7 TCC lines: T24, Biu87, EJ, J82, UM-UC-3, 5637, H-bc), a squamous carcinoma cell lines (SCaBER) and an immortalized benign cell line (SV-HUC-1).

A tri-drug combination was identified that showed significantly improved efficacy and reduced resistance as compared to other tested drug combinations and single drugs. Surprisingly, this tri-drug combination (EH/Ci/Mi or epirubicin hydrochloride/cisplatin/mitomycin) was greatly more effective and selective in killing a broad spectrum of cell lines than other combinations.

The EH/Ci/Mi regimen not only was more effective in cell killing, in terms of average cumulative cell survival (ACS: 6.32%), than other tri-drug regimens, but was also more effective than each individual drugs alone, even when they were dosed at four-fold levels: Ci (6000 ng/mL, ACS: 16.60%), Mi (800 ng/mL, ACS: 40.49%) or EH (1000 ng/mL, ACS: 9.11%), respectively. This result, therefore, is indicative of synergism of the three drugs for treating bladder cancer. Such synergism is shown as a negative interaction coefficient Hbc ACS (equation 3 below).

It is also noted that the EH/Ci/Mi regimen possessed both a broad spectrum of and highly specific anti-bladder cancer activity, killing between 82.86% and 99.52% bladder cancer cells in comparison to only 47.47% immortalized benign bladder epithelial cells. Further, preclinical in vivo verification revealed its markedly enhanced anti-tumor efficacy as compared to its bi- or mono-drug components in cell line derived tumor xenografts.

Another surprising and unexpected finding is that inclusion of gemcitabine (Ge) in a combination actually was detrimental to the combination's cancer cell-killing ability. Therefore, when selecting drug combinations from these drugs, gemcitabine can be avoided.

In accordance with one embodiment of the present disclosure, therefore, provided is a method for treating a human patient suffering from bladder cancer. In one aspect, the method entails administering to the patient an effective amount of mitomycin, or an analogue thereof, and an effective amount of a platinum drug (e.g., cisplatin, carboplatin, oxaliplatin, satraplatin, picoplatin, nedaplatin, triplatin, and lipoplatin). In one embodiment, the method further includes administering to the patient an effective amount of an anthracycline drug (e.g., epirubicin, pirarubicin, doxorubicin, daunorubicin, idarubicin, valrubicin, and mitoxantrone).

In some aspects, the patient is not being treated with gemcitabine. In some aspects, the patient is not being treated with paclitaxel or docetaxel. In some aspects, the patient is not being treated with fluorouracil (5-FU), methotrexate or vinblastine. In some aspects, the patient is not being treated with any other chemotherapeutic drugs. In some aspects, the patient is not being treated with any other drug that is not an analogue of mitomycin, a platinum drug, or an anthracycline drug.

In some aspects, the method does not include administering to the patient gemcitabine. In some aspects, the method does not include administering to the patient paclitaxel or docetaxel. In some aspects, the method does not include administering to the patient fluorouracil (5-FU), methotrexate or vinblastine. In some aspects, the method does not include administering to the patient any other chemotherapeutic drugs. In some aspects, the method does not include administering to the patient any other drug that is not an analogue of mitomycin, a platinum drug, or an anthracycline drug.

Mitomycin, also known as Mitomycin C (Mi), has a chemical name of [6-Amino-8a-methoxy-5-methyl-4,7-dioxo-1,1a,2,4,7,8,8a,8b-octahydroazireno [2',3':3,4] pyrrolo [1,2-a]indol-8-yl]methyl carbamate. Mitomycin is a potent DNA crosslinker, accomplished by reductive activation followed by two N-alkylations. Analogues of mitomycin include, without limitation, BMS-181174 (Macaulay et al., Br J Cancer. 1998 June; 77(11): 2020-2027), BMY 25282

(Wilson et al., Cancer Res., 45:5281-6 (1985)), and about 30 analogues disclosed in Kunz et al., *J Med Chem.* 1991 July; 34(7):2281-6.

Cisplatin is a platinum-containing anti-cancer drug ("platinum drug") and has a chemical name of (SP-4-2)-diamminedichloroplatinum(II). Carboplatin, or cis-Diammine(1,1-cyclobutanedicarboxylato) platinum(II), is also a platinum-containing anti-cancer drug and has reduced side-effects compared to its parent compound cisplatin. Oxaliplatin is another platinum-containing anti-cancer drug and has a chemical name of [(1R,2R)-cyclohexane-1,2-diamine] ethanedioato-O,O')platinum(II). Other platinum drugs include, without limitation, satraplatin, picoplatin, nedaplatin, triplatin, and lipoplatin.

Epirubicin, or epirubicin hydrochloride (EH), is an anthracycline drug. Epirubicin has a chemical name of (8R,10S)-10-((2S,4S,5R,6S)-4-amino-5-hydroxy-6-methyl-tetrahydro-2H-pyran-2-yl)-6,8,11-trihydroxy-8-(2-hydroxy-acetyl)-1-methoxy-7,8,9,10-tetrahydrotetracene-5,12-dione. Epirubicin acts by intercalating DNA strands. Intercalation results in complex formation which inhibits DNA and RNA synthesis. It also triggers DNA cleavage by topoisomerase II, resulting in mechanisms that lead to cell death.

Other example anthracycline drugs include daunorubicin, idarubicin, valrubicin, mitoxantrone, pirarubicin ((3S)-3-glycoloyl-3,5,12-trihydroxy-10-methoxy-6,11-dioxo-1,2,3,4,6,11-hexahydrotetracen-1-yl 3-amino-2,3,6-trideoxy-4-O-[(2R)-tetrahydro-2H-pyran-2-yl]-α-L-lyxo-hexopyranoside) and doxorubicin ((7S,9S)-7-[(2R,4S,5S,6S)-4-amino-5-hydroxy-6-methyloxan-2-yl]oxy-6,9,11-trihydroxy-9-(2-hydroxyacetyl)-4-methoxy-8,10-dihydro-7H-tetracene-5,12-dione).

In a particular embodiment, provided is a method for treating a human patient suffering from bladder cancer which method entails administering to the patient an effective amount of mitomycin, an effective amount of cisplatin, and an effective amount of epirubicin.

In one embodiment, the patient being treated is not undergoing treatment with another chemotherapeutic drug. In some aspects, the patient is not being treated with gemcitabine. In some aspects, the patient is not being treated with paclitaxel or docetaxel. Yet, in some aspects, the patient is not being treated with fluorouracil (5-FU), methotrexate or vinblastine.

In one aspect, the patient is further treated with radiation therapy and/or surgery.

Compositions for treating bladder cancers are also provided. In one embodiment, a composition is provided, comprising mitomycin or an analogue thereof, a platinum drug (e.g., cisplatin, carboplatin, oxaliplatin, satraplatin, picoplatin, nedaplatin, triplatin, and lipoplatin) and an anthracycline drug (e.g., epirubicin, pirarubicin, doxorubicin, daunorubicin, idarubicin, valrubicin, and mitoxantrone). In one aspect, the composition comprises mitomycin, cisplatin and epirubicin.

Kits and packages for treating bladder cancers are also provided. In one embodiment, a kit or package is provided, comprising mitomycin, a platinum drug (e.g., cisplatin, carboplatin, oxaliplatin, satraplatin, picoplatin, nedaplatin, triplatin, and lipoplatin) and an anthracycline drug (e.g., epirubicin, pirarubicin, doxorubicin, daunorubicin, idarubicin, valrubicin, and mitoxantrone). In one aspect, the kit or package comprises mitomycin, cisplatin and epirubicin.

In one embodiment, the composition does not include another chemotherapeutic drug. In some aspects, the composition does not include gemcitabine. In some aspects, the composition does not include paclitaxel or docetaxel. Yet, in some aspects, the composition does not include fluorouracil (5-FU), methotrexate or vinblastine.

Administration and Dosages

The chemotherapeutic agents or drugs can be administered as a composition. A "composition" typically intends a combination of the active agent and another carrier, e.g., compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars such as monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this disclosure, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional proviso that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", 52$^{nd}$ ed., Medical Economics, Montvale, N.J. (1998).

In another aspect of the disclosure, the method for treating a patient further includes surgical resection of a metastatic or non-metastatic solid malignant tumor and, in some aspects, in combination with radiation. Methods for treating these tumors as Stage I, Stage II, Stage III, or Stage IV by surgical resection and/or radiation are known to one skilled in the art. Guidelines describing methods for treatment by surgical resection and/or radiation can be found at the National Comprehensive Cancer Network's web site, nccn.org, last accessed on May 27, 2008.

The drugs or compositions can be administered by any suitable formulation. Accordingly, a formulation comprising the necessary therapy is further provided herein. The formulation can further comprise one or more preservatives or stabilizers. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, and 1.0%).

The disclosure provides an article of manufacture, comprising packaging material and at least one vial comprising a solution of the chemotherapy as described herein and/or or at least one antibody or its biological equivalent with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The disclosure further comprises an article of manufacture, comprising packaging material, a first vial comprising the chemotherapy and/or at least one lyophilized antibody or its biological equivalent and a second vial comprising an aqueous diluent of prescribed buffer or preservative, wherein said packaging material comprises a label that instructs a patient to reconstitute the therapeutic in the aqueous diluent to form a solution that can be held over a period of twenty-four hours or greater.

Chemotherapeutic formulations of the present disclosure can be prepared by a process which comprises mixing at least one antibody or biological equivalent and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing of the antibody and preservative in an aqueous diluent is carried out using conventional dissolution and mixing procedures. For example, a measured amount of at least one antibody in buffered solution is combined with the desired preservative in a buffered solution in quantities sufficient to provide the antibody and preservative at the desired concentrations. Variations of this process would be recognized by one of skill in the art, e.g., the order the components are added, whether additional additives are used, the temperature and pH at which the formulation is prepared, are all factors that can be optimized for the concentration and means of administration used.

The compositions and formulations can be provided to patients as clear solutions or as dual vials comprising a vial of lyophilized antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available. Recognized devices comprising these single vial systems include those pen-injector devices for delivery of a solution such as BD Pens, BD Autojectore, Humaject® NovoPen®, B-D® Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, e.g., as made or developed by Becton Dickensen (Franklin Lakes, N.J. available at bectondickenson.com), Disetronic (Burgdorf, Switzerland, available at disetronic.com; Bioject, Portland, Oreg. (available at bioject.com); National Medical Products, Weston Medical (Peterborough, UK, available at weston-medical.com), Medi-Ject Corp (Minneapolis, Minn., available at mediject.com).

Various delivery systems are known and can be used to administer a chemotherapeutic agent of the disclosure, e.g., encapsulation in liposomes, microparticles, microcapsules, expression by recombinant cells, receptor-mediated endocytosis. See e.g., Wu and Wu (1987) J. Biol. Chem. 262: 4429-4432 for construction of a therapeutic nucleic acid as part of a retroviral or other vector, etc. Methods of delivery include but are not limited to intra-arterial, intra-muscular, intravenous, intranasal and oral routes. In a specific embodiment, it may be desirable to administer the pharmaceutical compositions of the disclosure locally to the area in need of treatment; this may be achieved by, for example, and not by way of limitation, local infusion during surgery, by injection or by means of a catheter.

The agents identified herein as effective for their intended purpose can be administered to subjects or individuals identified by the methods herein as suitable for the therapy. Therapeutic amounts can be empirically determined and will vary with the pathology being treated, the subject being treated and the efficacy and toxicity of the agent.

Methods of administering pharmaceutical compositions are well known to those of ordinary skill in the art and include, but are not limited to, oral, intravesical instillation, injection, intravenous or parenteral administration. Administration can be effected continuously or intermittently throughout the course of the treatment. Methods of determining the most effective means and dosage of administration are well known to those of skill in the art and will vary with the cancer being treated and the patient and the subject being treated. Single or multiple administrations can be carried out with the dose level and pattern being selected by the treating physician. In one embodiment, one or more of the drugs of the presently disclosed combinations is administered intravesically.

In one aspect, the mitomycin is administered intravesically. In one aspect, the mitomycin is administered orally or intravenously. A suitable dose ranges from 5 mg to 60 mg per treatment, per administration, or per day. In one aspect, the dose range is 5 mg to 50 mg, 5 mg to 40 mg, 5 mg to 30 mg, 5 mg to 20 mg, 5 mg to 10 mg, 10 mg to 60 mg, 10 mg to 50 mg, 10 mg to 40 mg, 10 mg to 30 mg, 10 mg to 20 mg, 20 mg to 60 mg, 20 mg to 50 mg, 20 mg to 40 mg, 20 mg to 30 mg, 30 mg to 60 mg, 30 mg to 50 mg, or 30 mg to 40.

In one aspect, the platinum drug is administered intravesically. In one aspect, the platinum drug is administered orally or intravenously. A suitable dose ranges from 10 mg to 200 mg per treatment, per administration, or per day. In one aspect, the dose range is 10 mg to 150 mg, 10 mg to 120 mg, 10 mg to 100 mg, 10 mg to 90 mg, 10 mg to 80 mg, 10 mg to 70 mg, 10 mg to 60 mg, 10 mg to 50 mg, 20 mg to 150 mg, 20 mg to 120 mg, 20 mg to 100 mg, 20 mg to 90 mg, 20 mg to 80 mg, 20 mg to 70 mg, 20 mg to 60 mg, 20 mg to 50 mg, 30 mg to 150 mg, 30 mg to 120 mg, 30 mg to 100 mg, 30 mg to 90 mg, 30 mg to 80 mg, 30 mg to 70 mg, 30 mg to 60 mg, 30 mg to 50 mg, 40 mg to 150 mg, 40 mg to 120 mg, 40 mg to 100 mg, 40 mg to 90 mg, 40 mg to 80 mg, 40 mg to 70 mg, 40 mg to 60 mg, 40 mg to 50 mg, 50 mg to 150 mg, 50 mg to 120 mg, 50 mg to 100 mg, 50 mg to 90 mg, 50 mg to 80 mg, 50 mg to 70 mg, 50 mg to 60 mg, 60 mg to 150 mg, 60 mg to 120 mg, 60 mg to 100 mg, 60 mg to 90 mg, 60 mg to 80 mg, 60 mg to 70 mg, 70 mg to 150 mg, 70 mg to 120 mg, 70 mg to 100 mg, 70 mg to 90 mg, 70 mg to 80 mg, 80 mg to 150 mg, 80 mg to 120 mg, 80 mg to 100 mg, 80 mg to 90 mg, 90 mg to 200 mg, 90 mg to 100 mg, 100 mg to 200 mg, 100 mg to 150 mg, or 100 mg to 120 mg.

In one aspect, the cisplatin is administered intravesically. In one aspect, the cisplatin is administered orally or intravenously. A suitable dose ranges from 10 mg to 200 mg per treatment, per administration, or per day. In one aspect, the dose range is 10 mg to 150 mg, 10 mg to 120 mg, 10 mg to 100 mg, 10 mg to 90 mg, 10 mg to 80 mg, 10 mg to 70 mg, 10 mg to 60 mg, 10 mg to 50 mg, 20 mg to 150 mg, 20 mg to 120 mg, 20 mg to 100 mg, 20 mg to 90 mg, 20 mg to 80 mg, 20 mg to 70 mg, 20 mg to 60 mg, 20 mg to 50 mg, 30 mg to 150 mg, 30 mg to 120 mg, 30 mg to 100 mg, 30 mg to 90 mg, 30 mg to 80 mg, 30 mg to 70 mg, 30 mg to 60 mg, 30 mg to 50 mg, 40 mg to 150 mg, 40 mg to 120 mg, 40 mg to 100 mg, 40 mg to 90 mg, 40 mg to 80 mg, 40 mg to 70 mg, 40 mg to 60 mg, 40 mg to 50 mg, 50 mg to 150 mg, 50 mg to 120 mg, 50 mg to 100 mg, 50 mg to 90 mg, 50 mg to 80 mg, 50 mg to 70 mg, 50 mg to 60 mg, 60 mg to 150 mg, 60 mg to 120 mg, 60 mg to 100 mg, 60 mg to 90 mg, 60 mg to 80 mg, 60 mg to 70 mg, 70 mg to 150 mg, 70 mg to 120 mg, 70 mg to 100 mg, 70 mg to 90 mg, 70 mg to 80 mg, 80 mg to 150 mg, 80 mg to 120 mg, 80 mg to 100 mg, 80 mg to 90 mg, 90 mg to 200 mg, 90 mg to 100 mg, 100 mg to 200 mg, 100 mg to 150 mg, or 100 mg to 120 mg.

In one aspect, the anthracycline drug is administered intravesically. In one aspect, the anthracycline drug is administered orally or intravenously. A suitable dose ranges from 1 mg to 200 mg per treatment, per administration, or per day. In one aspect, the dose range is 1 mg to 150 mg, 1 mg to 120 mg, 1 mg to 100 mg, 1 mg to 90 mg, 1 mg to 80 mg, 1 mg to 70 mg, 1 mg to 60 mg, 1 mg to 50 mg, 1 mg to 40 mg, 1 mg to 30 mg, 1 mg to 20 mg, 2 mg to 150 mg, 2 mg to 120 mg, 2 mg to 100 mg, 2 mg to 90 mg, 2 mg to 80 mg, 2 mg to 70 mg, 2 mg to 60 mg, 2 mg to 50 mg, 2 mg to 40 mg, 1 mg to 30 mg, 2 mg to 20 mg, 3 mg to 150 mg, 3 mg to 120 mg, 3 mg to 100 mg, 3 mg to 90 mg, 3 mg to 80 mg, 3 mg to 70 mg, 3 mg to 60 mg, 3 mg to 50 mg, 3 mg to 40 mg, 1 mg to 30 mg, 3 mg to 20 mg, 4 mg to 150 mg, 4 mg to 120 mg, 4 mg to 100 mg, 4 mg to 90 mg, 4 mg to 80 mg, 4 mg to 70 mg, 4 mg to 60 mg, 4 mg to 50 mg, 4 mg to 40 mg, 1 mg to 30 mg, 4 mg to 20 mg, 5 mg to 150 mg, 5 mg to 120 mg, 5 mg to 100 mg, 5 mg to 90 mg, 5 mg to 80 mg, 5 mg to 70 mg, 5 mg to 60 mg, 5 mg to 50 mg, 5 mg to 40 mg, 1 mg to 30 mg, 5 mg to 20 mg, 10 mg to 150 mg, 10 mg to 120 mg, 10 mg to 100 mg, 10 mg to 90 mg, 10 mg to 80 mg, 10 mg to 70 mg, 10 mg to 60 mg, 10 mg to 50 mg, 20 mg to 150 mg, 20 mg to 120 mg, 20 mg to 100 mg, 20 mg to 90 mg, 20 mg to 80 mg, 20 mg to 70 mg, 20 mg to 60 mg, 20 mg to 50 mg, 30 mg to 150 mg, 30 mg to 120 mg, 30 mg to 100 mg, 30 mg to 90 mg, 30 mg to 80 mg, 30 mg to 70 mg, 30 mg to 60 mg, 30 mg to 50 mg, 40 mg to 150 mg, 40 mg to 120 mg, 40 mg to 100 mg, 40 mg to 90 mg, 40 mg to 80 mg, 40 mg to 70 mg, 40 mg to 60 mg, 40 mg to 50 mg, 50 mg to 150 mg, 50 mg to 120 mg, 50 mg to 100 mg, 50 mg to 90 mg, 50 mg to 80 mg, 50 mg to 70 mg, 50 mg to 60 mg, 60 mg to 150 mg, 60 mg to 120 mg, 60 mg to 100 mg, 60 mg to 90 mg, 60 mg to 80 mg, 60 mg to 70 mg, 70 mg to 150 mg, 70 mg to 120 mg, 70 mg to 100 mg, 70 mg to 90 mg, 70 mg to 80 mg, 80 mg to 150 mg, 80 mg to 120 mg, 80 mg to 100 mg, 80 mg to 90 mg, 90 mg to 200 mg, 90 mg to 100 mg, 100 mg to 200 mg, 100 mg to 150 mg, or 100 mg to 120 mg.

In one aspect, the epirubicin is administered intravesically. In one aspect, the epirubicin is administered orally or intravenously A suitable dose ranges from 1 mg to 200 mg per treatment, per administration, or per day. In one aspect, the dose range is 1 mg to 150 mg, 1 mg to 120 mg, 1 mg to 100 mg, 1 mg to 90 mg, 1 mg to 80 mg, 1 mg to 70 mg, 1 mg to 60 mg, 1 mg to 50 mg, 1 mg to 40 mg, 1 mg to 30 mg, 1 mg to 20 mg, 2 mg to 150 mg, 2 mg to 120 mg, 2 mg to 100 mg, 2 mg to 90 mg, 2 mg to 80 mg, 2 mg to 70 mg, 2 mg to 60 mg, 2 mg to 50 mg, 2 mg to 40 mg, 1 mg to 30 mg, 2 mg to 20 mg, 3 mg to 150 mg, 3 mg to 120 mg, 3 mg to 100 mg, 3 mg to 90 mg, 3 mg to 80 mg, 3 mg to 70 mg, 3 mg to 60 mg, 3 mg to 50 mg, 3 mg to 40 mg, 1 mg to 30 mg, 3 mg to 20 mg, 4 mg to 150 mg, 4 mg to 120 mg, 4 mg to 100 mg, 4 mg to 90 mg, 4 mg to 80 mg, 4 mg to 70 mg, 4 mg to 60 mg, 4 mg to 50 mg, 4 mg to 40 mg, 1 mg to 30 mg, 4 mg to 20 mg, 5 mg to 150 mg, 5 mg to 120 mg, 5 mg to 100 mg, 5 mg to 90 mg, 5 mg to 80 mg, 5 mg to 70 mg, 5 mg to 60 mg, 5 mg to 50 mg, 5 mg to 40 mg, 1 mg to 30 mg, 5 mg to 20 mg, 10 mg to 150 mg, 10 mg to 120 mg, 10 mg to 100 mg, 10 mg to 90 mg, 10 mg to 80 mg, 10 mg to 70 mg, 10 mg to 60 mg, 10 mg to 50 mg, 20 mg to 150 mg, 20 mg to 120 mg, 20 mg to 100 mg, 20 mg to 90 mg, 20 mg to 80 mg, 20 mg to 70 mg, 20 mg to 60 mg, 20 mg to 50 mg, 30 mg to 150 mg, 30 mg to 120 mg, 30 mg to 100 mg, 30 mg to 90 mg, 30 mg to 80 mg, 30 mg to 70 mg, 30 mg to 60 mg, 30 mg to 50 mg, 40 mg to 150 mg, 40 mg to 120 mg, 40 mg to 100 mg, 40 mg to 90 mg, 40 mg to 80 mg, 40 mg to 70 mg, 40 mg to 60 mg, 40 mg to 50 mg, 50 mg to 150 mg, 50 mg to 120 mg, 50 mg to 100 mg, 50 mg to 90 mg, 50 mg to 80 mg, 50 mg to 70 mg, 50 mg to 60 mg, 60 mg to 150 mg, 60 mg to 120 mg, 60 mg to 100 mg, 60 mg to 90 mg, 60 mg to 80 mg, 60 mg to 70 mg, 70 mg to 150 mg, 70 mg to 120 mg, 70 mg to 100 mg, 70 mg to 90 mg, 70 mg to 80 mg, 80 mg to 150 mg, 80 mg to 120 mg, 80 mg to 100 mg, 80 mg to 90 mg, 90 mg to 200 mg, 90 mg to 100 mg, 100 mg to 200 mg, 100 mg to 150 mg, or 100 mg to 120 mg.

In one aspect, the epirubicin is administered intravesically and a suitable concentration range can be from 0.5 mg/mL to 2 mg/mL. In one aspect, the suitable concentration is from 0.5 mg/mL to 1.8 mg/mL, from 0.5 mg/mL to 1.5 mg/mL, from 0.5 mg/mL to 1.2 mg/mL, from 0.75 mg/mL to 1.2 mg/mL, from 0.5 mg/mL to 1.0 mg/mL, from 0.5 mg/mL to 0.75 mg/mL, or from 0.75 mg/mL to 1.0 mg/mL.

Each drug of the combinations can be administered separately (sequentially or concurrently through each of its suitable administration route) or together.

Bladder cancers suitable for the presently disclosed treatments include, without limitation, transitional cell carcinoma (e.g., superficial bladder cancer, invasive bladder cancer, and metastatic bladder cancer), squamous cell carcinoma, adenocarcinoma, and small cell bladder cancer.

The presently disclosed compositions and methods can also be suitable for treating different types of bladder cancer at various stages, such as:

Stage 0 or I: The cancer is contained; the cancer cells have not grown beyond the inner lining of the bladder (Stage 0) or beyond the layer of tissue supporting the inner lining of the bladder (Stage I). The cancer has not extended into the muscle or out into lymph nodes. The five-year survival rate for Stage 0 bladder cancer is 95 percent while that for Stage I is 85 percent, according to the American Cancer Society.

Stage II: The cancer cells have spread to the muscle layer; this stage of bladder cancer has a five-year survival rate of approximately 55 percent.

Stage III: Cancer has spread outside the bladder to the fat separating the bladder from other organs, resulting in a five-year survival rate of 38 percent.

Stage IV: Cancer cells have spread to other organs, reducing the five-year survival rate to 16 percent.

The disclosure now being generally described, it will be more readily understood by reference to the following example which is included merely for purposes of illustration of certain aspects and embodiments of the present disclosure, and are not intended to limit the disclosure.

EXPERIMENTAL EXAMPLES

Example 1

Therapeutic outcomes of combination chemotherapy have not significantly advanced during past decades, which has been attributed to the formidable challenges of optimizing drug combinations. Testing a matrix of all possible combinations of doses and agents in a single cell line, much less in multiple cell lines, is unfeasible due to virtually infinite number of possibilities.

This example utilizes a Feedback System Control (FSC) platform, a phenotype oriented approach to test 100 options among 15,625 possible combinations in a four-round of testing to identify an optimal drug combination in eight chemo-resistant distinct bladder cancer cell lines. This resulting tri-drug combination killed between 82.86% and 99.52% bladder cancer (BCa) cells, but only 47.47% immortalized benign bladder epithelial cells. Preclinical in vivo verification revealed its markedly enhanced anti-tumor efficacy as compared to its bi- or mono-drug components in cell line derived tumor xenografts. The collective response of these pathways to component drugs is both cell type- and drug type-specific. However, the entire spectrum of pathways triggered by the tri-drug regimen was similar in all four cancer cell lines, highlighting its broad spectrum killing of BCa lines, but not its component drugs. These findings underscore the FSC platform's promise for optimization of anti-cancer combination chemotherapies. More importantly, the resulting optimal drug combinations show great promise in the treatment of bladder cancer.

Introduction

Although there have been significant advances in the understanding of the molecular basis of cancer and several hundred-targeted therapeutics were introduced based on these discoveries, chemotherapeutic regimens that are the mainstay of cancer treatment remains largely unchanged. Most anticancer drugs have narrow therapeutic indices, leading to suboptimal dosing, treatment delay or discontinuance and reduced patient compliance to therapy. The idea of combination chemotherapy using two or more drugs that have no overlapping anti-cancer activities and systemic toxicities was first introduced in the late 70's. This approach has improved the cure rate for Hodgkin's lymphoma from 20 to 80% and for lymph sarcoma from 15% to over 50%. Since then, combination chemotherapy has gradually replaced single drug therapy in cancer. Nevertheless, improvements to chemotherapy in the last five decades have been slow.

One of the key challenges is that the current combination chemotherapy regimens are often derived from retrospective analyses of clinical trials and cell culture-based assays with an inadequate capacity to assess all possible combinations that vary in the number, type and doses of drugs, while simultaneously optimizing for multiple conditions (e.g. efficacy and safety). Cell-based optimization efforts assisted by mathematical methods were introduced in the late 90s. Additional approaches include the classical isobologram method, the "envelope of additivity" method to distinguish cytotoxic agents that are not significantly interacting and the Median effect analysis method introduced by Chou and Talalay. One limitation of all current methods is that they are limited to bi-drug interactions, despite of the fact that the majority of the combination regimens used in clinics today involve three or more drugs.

An obvious but prohibitive approach is the testing of all possible combinations of all drugs at all doses for the best regimen of the markedly improved therapeutic index. However, an effort of this kind exceeds the screening capacity of biomedical research laboratories today. Moreover, the extensive heterogeneity at the genetic, epigenetic, expressional and phenotypic levels of cancer cells in patients necessitates testing a large number of cancer cell lines in order to represent disease diversity, which further amplifies the task.

Bladder cancer (BCa) is the fourth most common type of tumors in male worldwide. Notorious for its recurrence and refractoriness to chemotherapy, BCa is one of the most difficult and costly malignancies. Treatments for muscle-invasive bladder cancer have not advanced beyond cisplatin-centered combination chemotherapy and surgery in the past 30 years. Median survival for patients with recurrent or metastatic bladder cancer remains 14-15 months. A recent multi-omic analysis of 131 bladder cancer patient samples has produced a comprehensive picture of the genetic defects and expression abnormalities associated with BCa, but few clues have been offered for better diagnostic and therapeutic opportunities. Pathologically, bladder cancer consists of two major types: transitional cell carcinoma (TCC) accounting for more than 90% and squamous cell carcinoma for 6% to 8% cases.

This example used a Feedback System Control (FSC) platform, a guided experimental optimizing process, to search for multi-drug combinations (FIG. 1). With the FSC, this example needed testing of less than 1% of all the possible combinations. This example used this platform to quickly select an effective tri-drug combination that is capable of killing seven TCC and one squamous cancer cell lines that essentially represent the clinical spectrum of bladder cancer. In contrast, this regimen possesses a significantly lower killing capability on an immortalized benign epithelial cell, an indication of its broad-spectrum cytotoxicity being cancer cell specific. It also more effectively suppressed the in vivo growth of three BCa-cell-line-derived-tumor-xenografts in nude mice than its mono- or bi-drug constituents.

By determining the activities of nine cancer-associated pathways in both bladder cancer and normal cell lines, this example showed that the collective response of these pathways to the single component drug of the tri-drug combination varies between drugs and between cell types. However, the entire spectrum of pathways activated by the tri-drug regimen was similar in all four cancer cell lines, explaining why the tri-drug combination has a broad anti-cancer effects but none of its component drug fails. The broad applicability of FSC for the optimal drug combinations to a wide range of disease indication is therefore anticipated.

List of Abbreviations

| Abbreviation | Original name |
|---|---|
| ACS | Average cumulative cell survival |
| Ci | Cisplatine |
| EH | Epirubicin Hydrochloride |
| Ge | Gemcitabine |
| Mi | Mitomycin |
| Pa | Paclitaxel |
| Pi | Pirarubicin |
| TCC | Transitional cell carcinoma |
| IC50 | Drug concentration for 50% cells killed |
| MTT | Test by thiazolyl blue tetrazolium blue |
| IHC | Immunohistochemistry |
| PBS | Phosphate balanced solution |

Methods

Experimental Design.

Each experiment was performed three times. All animals were adult BALB/C male nude mice of 8-12 weeks of age and experiments were performed in accordance with the National Institutes of Health Guide for the Care and Use of Laboratory Animals and approved by the animal research committee of Harbin Medical University, China.

Cell Culture Conditions and Treatments.

Cell lines (Table S1) used in this study included a normal uroepithelium cell line, SV-HUC-1, six muscles invasive (EJ, J82, UM-UC-3, T24, 5637 and H-bc) bladder cancer cell lines, one superficial transitional bladder cancer cell lines (Biu87), and a squamous-cell carcinoma cell line (SCaBER).

The clinical grade of the chemotherapeutics (NCI Dictionary of Cancer Terms) was provided by the First Affiliated Hospital of Harbin Medical University: Pirarubicin (Pi, Wanle, Shenzhen), Paclitaxel (Pa, Taiji, Sichuan), Adriamycin (Ad, Pfizer, Jiangsu), Epirubicin Hydrochloride (EH, Haizheng, Zhejiang), Hydroxycamptothecin (Hy, Lishizhen, Hubei), Cisplatin (Ci, Haosen, Jiangsu), Gemcitabine (Ge, Haosen, Jiangsu) and Mitomycin (Mi, Haizheng, Zhejiang). The drug induced cell death was determined by a thiazolyl blue tetrazolium blue (MTT, 490 nm reading) based cell proliferation assay in the cultured cells following treatment by various concentrations of drugs for 72 hours. The relative chemoresistance to each drug of all cell lines was calculated with the lowest $IC_{50}$ as a reference. The overall chemoresistance of each cell line was described as "chemoresistance index", the numerator of the total relative $IC_{50}$ to all the drugs over the number of drugs to rank the overall resistance state of each cell line to the six chemotherapeutics collectively.

Optimization of the Tri-Drug Regimen Via the FSC Platform in Eight BCa Cell Lines The "Differential Evolution" algorithm guided experimental optimization (DE) consisted of three iterative operations: generating drug combinations of experimental testing, acquiring the efficacy of the generated drug combinations with biological assays and recalculating further improved drug combinations using a feedback search algorithm. This example first tested twenty drug combinations at randomized doses. These drug combinations were generated from a random integer matrix generator, coded in MATLAB™ language. These twenty drug combinations were then experimentally tested for cancer cell cytotoxicity. The experimental data were then subjected to calculation with a DE algorithm for new drug combinations based on three major mathematical calculations: "Mutation", "Crossover" and "Selection". The equations for each step can be found in the main test. The equations for each step are coded in MATLAB™ language.

Statistical Modeling on the Relationships Between Cell Survivals and Drug Doses

Statistical analysis of experimentally measured cell survival rate was done for each individual cell line. The readouts (ACS) from 100 tested options for each cell line were pooled together and a polynomial regression model was built. The polynomial regression modeling is commonly used to mathematically describe the relationship between Y's (in this case, the cell death) and X's (in this case, the drug doses) using R language environment. The polynomial regression model was computed by function "g=lm{stats}" and simplified by function "g=step(stats)" in R programming.

The Pathway Analysis

The pathway analysis was performed with Qiagen's Cignal Finder Pathway Reporter Array systems according to the manufacturer's instructions. The pathway-focused dual-luciferase reporter construct was a mixture of an inducible transcription factor responsive firefly luciferase reporter and constitutively expressing renilla construct. Transcriptional response element (TRE) sequence response elements to each specific transcriptional factor triggered by the different signaling pathways are positioned before the TATA box of firefly luciferase reporter gene. The extent of activity of the reporter reflects the level of activity of the particular signaling pathway. CMV controlled renilla expression vector is co-transfected into the cell as an internal control. Non-inducible reporter construct that lacks the transcriptional factor binding sequence and could not be induced by any transcription factors is used as a negative control. Cells transfected with CMV directed firefly luciferase reporter gene serve as a positive control. Briefly, cells seeded in 6-well plates were transfected with Cignal finder pathway arrays according to the manufacturer's instructions (Qiagen). Then cells were seeded onto 96-well plates. Ci (6000 ng/mL), Mi (800 ng/mL), or EH (1000 ng/mL) and Ci/Mi/EH combination (Ci, 1500 ng/mL, Mi, 800 ng/mL and EH, 1000 ng/m L) were then added to the cells 24 h post-transfection. After 6 h of incubation with the different drugs at 37° C., cells were lysed and a dual luciferase assay (for firefly and renilla luciferase) was performed using a PromegaGloMax 20/20 illuminometer. The firefly luciferase activities were normalized over the renilla luciferase activities after background activity determined by luciferase activities of negative controls was subtracted. A triple test of cell survival under these drug doses was also performed by MTT assay following 18 h incubation at 37° C.

Pearson Correlation Analysis of the Signaling Pathway Data in Chemo-Resistant Distinct Cell Lines The levels of pathway activities were digitized as follows: activated (1): if pathway activity was higher than 1.5-fold over the activity in 5637 cells (Table 4A) or than the no-drug control; repressed (−1), if the activity was 0.5-fold lower than in 5637 cells (Table 4B) or than the no-drug control, and null (0) if neither of the above holds. Correlation coefficients between two cell lines or between drug-treated cells and untreated were calculated (Table 4). The definition and calculation equations for correlation coefficients can be found in the main text. To calculate the correlation coefficients between the two cell lines, the R language statistics function "cor{stats}" was used to generate the correlation matrix between multiple cell lines.

TABLE 1

The 1st round of iteration. The combinations (1-20) vary with the dose (ng/mL) of six drugs and have different effects on the cell survival (%). The ACS (%) summarized from the cell survival of each cell line under the treatment of each combination.

|  |  | Combinations ||||||||||
|---|---|---|---|---|---|---|---|---|---|---|---|
|  |  | 1 | 2 | 3 | 4 | 5 | 6 | 7 | 8 | 9 | 10 |
| Drug concentration (ng/ml) | Pi | 1.6 | 8 | 8 | 1.6 | 8 | 0.32 | 40 | 0.32 | 0.32 | 8 |
|  | Pa | 32 | 6.4 | 32 | 1.28 | 32 | 160 | 1.28 | 6.4 | 6.4 | 160 |
|  | EH | 10 | 2 | 50 | 10 | 50 | 10 | 50 | 250 | 10 | 10 |
|  | Ci | 300 | 300 | 300 | 12 | 60 | 1500 | 60 | 1500 | 300 | 12 |
|  | Ge | 5 | 1 | 0.04 | 5 | 5 | 0.2 | 0.2 | 1 | 0.2 | 0.2 |
|  | Mi | 8 | 8 | 8 | 8 | 40 | 1000 | 200 | 1000 | 1000 | 200 |
| Cell survival (%) | 5637 | 24.58 | 43.82 | 45.43 | 65.40 | 42.03 | 1.23 | 26.47 | 0.51 | 11.57 | 16.17 |
|  | H-bc | 52.57 | 56.01 | 52.30 | 59.60 | 58.01 | 18.96 | 48.40 | 3.40 | 42.60 | 51.76 |
|  | J-82 | 43.69 | 55.27 | 50.62 | 72.9 | 46.08 | 6.07 | 32.91 | 6.62 | 11.53 | 26.82 |
|  | T24 | 36.41 | 44.71 | 45.20 | 62.06 | 39.05 | 7.97 | 32.91 | 11.67 | 20.07 | 29.74 |
|  | EJ | 46.55 | 51.31 | 40.41 | 69.1 | 41.61 | 30.67 | 37.67 | 21.79 | 35.01 | 36.4 |
|  | Biu87 | 21.67 | 49.15 | 51.1 | 26.78 | 31.5 | 7.64 | 48.37 | 16.09 | 20.32 | 37.65 |
|  | ACS (%) | 37.58 | 50.04 | 47.51 | 59.31 | 43.05 | 12.09 | 36.26 | 10.01 | 23.52 | 33.09 |

|  |  | Combinations ||||||||||
|---|---|---|---|---|---|---|---|---|---|---|---|
|  |  | 11 | 12 | 13 | 14 | 15 | 16 | 17 | 18 | 19 | 20 |
| Drug concentration (ng/ml) | Pi | 1.6 | 8 | 40 | 40 | 0.32 | 40 | 40 | 8 | 1.6 | 8 |
|  | Pa | 1.28 | 160 | 1.28 | 1.28 | 1.28 | 1.28 | 32 | 6.4 | 6.4 | 1.28 |
|  | EH | 50 | 50 | 250 | 250 | 10 | 50 | 50 | 50 | 250 | 2 |
|  | Ci | 60 | 1500 | 300 | 60 | 1500 | 12 | 1500 | 1500 | 1500 | 300 |
|  | Ge | 0.04 | 5 | 5 | 0.04 | 1 | 1 | 5 | 5 | 0.2 | 0.04 |
|  | Mi | 8 | 40 | 40 | 8 | 40 | 200 | 200 | 8 | 200 | 40 |
| Cell survival (%) | 5637 | 62.93 | 13.59 | 26.19 | 47.21 | 30.10 | 25.27 | 6.62 | 23.94 | 1.99 | 48.26 |
|  | H-bc | 57.78 | 26.84 | 30.01 | 33.02 | 33.64 | 44.03 | 15.80 | 29.12 | 5.48 | 58.13 |
|  | J-82 | 65.16 | 13.4 | 18.67 | 31 | 24.3 | 24.77 | 7.63 | 16.23 | 8.26 | 56.8 |
|  | T24 | 61.60 | 14.80 | 17.25 | 24.05 | 22.03 | 34.08 | 11.21 | 15.78 | 8.73 | 39.38 |
|  | EJ | 56.02 | 36.62 | 22.28 | 28.35 | 45.2 | 34.79 | 31.27 | 37.86 | 23.63 | 53.67 |
|  | Biu87 | 72.26 | 8.56 | 17.59 | 33.22 | 14.02 | 45.38 | 12.87 | 14.05 | 13.3 | 65.93 |
|  | ACS (%) | 62.63 | 18.97 | 22.00 | 32.81 | 28.21 | 34.72 | 14.23 | 22.83 | 10.23 | 53.70 |

TABLE 2

The 4th round of iteration. The combinations (1-40) vary with the dose (ng/mL) of six drugs and have different effects on the cell survival (%). The ACS (%) summarized from the cell survival of each cell line under the treatment for combination.

| | | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| Drug Concentration (ng/ml) | Pi | 40 | 8 | 8 | 40 | 0 | 0 | 1.6 | 0 | 0 | 40 | 1.6 | 1.6 | 1.6 | 1.6 | 1.6 | 8 | 8 | 0.32 | 8 | 8 |
| | Pa | 160 | 6.4 | 0 | 1.28 | 160 | 1.28 | 50 | 0 | 0 | 160 | 160 | 0 | 6.4 | 0 | 0 | 6.4 | 6.4 | 32 | 160 | 0 |
| | EH | 250 | 250 | 50 | 50 | 250 | 50 | 50 | 50 | 250 | 0 | 2 | 2 | 2 | 2 | 50 | 2 | 50 | 50 | 0 | 0 |
| | Ci | 1500 | 12 | 60 | 300 | 1500 | 60 | 1500 | 60 | 1500 | 1500 | 300 | 1500 | 1500 | 0 | 0 | 60 | 60 | 300 | 1500 | 300 |
| | Ge | 0 | 0 | 1 | 0.2 | 0 | 0 | 5 | 5 | 0.2 | 5 | 0.04 | 1 | 1 | 0.2 | 5 | 0.2 | 5 | 0.2 | 5 | 0.2 |
| | Mi | 1000 | 200 | 200 | 1000 | 1000 | 8 | 8 | 8 | 8 | 5 | 8 | 0 | 40 | 200 | 8 | 1000 | 200 | 0 | 0 | 1000 |
| Cell survival (%) | Biu87 | 1.06 | 13.15 | 10.83 | 3.44 | 1.76 | 67.33 | 2.49 | 19.33 | 4.74 | 2.33 | 19.08 | 3.03 | 3.98 | 11.15 | 16.07 | 4.11 | 4.84 | 32.59 | 2.01 | 2.97 |
| | J-82 | 1.09 | 16.03 | 24.08 | 3.20 | 1.55 | 81.67 | 10.85 | 83.10 | 11.47 | 9.01 | 46.99 | 17.53 | 13.42 | 22.31 | 83.37 | 5.41 | 15.91 | 55.90 | 11.47 | 3.26 |
| | EJ | 10.47 | 33.23 | 44.31 | 20.32 | 13.79 | 95.23 | 49.72 | 89.61 | 48.27 | 39.92 | 65.19 | 59.73 | 51.97 | 42.01 | 86.61 | 23.16 | 37.99 | 73.87 | 49.02 | 18.98 |
| | ACCS (%) | 4.21 | 20.80 | 26.41 | 8.99 | 5.70 | 81.41 | 21.02 | 64.01 | 21.49 | 17.09 | 43.75 | 26.76 | 23.12 | 25.16 | 62.02 | 10.89 | 19.58 | 54.12 | 20.83 | 8.40 |
| | 5637 | 12.67 | — | — | 49.82 | 31.48 | — | 58.46 | — | 54.30 | 54.91 | — | — | — | — | — | 58.89 | 63.70 | — | 59.90 | 58.19 |
| | T24 | 6.71 | — | — | 6.07 | 6.53 | — | 67.09 | — | 60.35 | 64.83 | — | — | — | — | — | 14.88 | 32.74 | — | 62.31 | 11.91 |
| | UM-UC-3 | 4.66 | — | — | 19.97 | 11.74 | — | 39.16 | — | 35.24 | 25.80 | — | — | — | — | — | 19.74 | 31.35 | — | 34.55 | 44.89 |
| | H-bc | 0.08 | — | — | 69.34 | 1.83 | — | 79.74 | — | 73.68 | 72.95 | — | — | — | — | — | 76.52 | 77.57 | — | 69.74 | 72.60 |
| | ACS (%) | 4.59 | — | — | 21.52 | 8.58 | — | 38.44 | — | 36.01 | 33.72 | — | — | — | — | — | 25.34 | 33.01 | — | 36.13 | 26.60 |

| | | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|
| Drug Concentration (ng/ml) | Pi | 0 | 40 | 8 | 40 | 40 | 0 | 0 | 40 | 40 | 40 | 0 | 0 | 0 | 8 | 8 | 1.6 | 40 | 0 | 8 | 0 |
| | Pa | 32 | 0 | 160 | 0 | 0 | 32 | 0 | 0 | 160 | 32 | 160 | 6.4 | 0 | 0 | 0 | 160 | 0 | 32 | 0 | 0 |
| | EH | 2 | 50 | 0 | 250 | 250 | 50 | 10 | 50 | 50 | 0 | 10 | 0 | 10 | 50 | 0 | 2 | 50 | 250 | 50 | 250 |
| | Ci | 300 | 12 | 0 | 300 | 60 | 0 | 1500 | 0 | 300 | 12 | 1500 | 1500 | 0 | 1500 | 1500 | 0.2 | 1500 | 1500 | 1500 | 1500 |
| | Ge | 5 | 0 | 0.2 | 5 | 0 | 5 | 1 | 1 | 5 | 0 | 0.2 | 1 | 5 | 0.2 | 5 | 0.2 | 5 | 0.2 | 5 | 0 |
| | Mi | 0 | 200 | 200 | 40 | 0 | 1000 | 1500 | 200 | 200 | 1000 | 0 | 1000 | 1000 | 1000 | 40 | 1000 | 1000 | 1000 | 40 | 200 |
| Cell survival (%) | Biu87 | 11.37 | 13.41 | 13.91 | 5.62 | 19.78 | 2.76 | 4.77 | 12.09 | 5.70 | 6.88 | 2.83 | 1.70 | 2.42 | 1.41 | 2.23 | 3.39 | 1.73 | 2.01 | 3.74 | 2.17 |
| | J-82 | 69.36 | 21.93 | 24.21 | 25.25 | 65.75 | 8.46 | 20.82 | 28.68 | 19.46 | 9.93 | 15.54 | 2.21 | 9.93 | 1.86 | 12.82 | 8.68 | 1.71 | 1.61 | 12.36 | 7.14 |
| | EJ | 77.62 | 36.29 | 36.91 | 44.56 | 66.58 | 25.51 | 63.19 | 37.58 | 39.91 | 20.74 | 40.61 | 15.55 | 26.85 | 16.89 | 47.02 | 21.00 | 13.66 | 15.55 | 48.61 | 28.13 |
| | ACCS (%) | 52.78 | 23.88 | 25.01 | 25.14 | 50.70 | 12.25 | 29.60 | 26.11 | 21.69 | 12.51 | 19.66 | 6.49 | 13.06 | 6.72 | 20.69 | 11.02 | 5.70 | 6.39 | 21.57 | 12.48 |
| | 5637 | — | — | — | — | — | 55.04 | — | — | — | 55.21 | 56.03 | 41.74 | 67.91 | 38.98 | 72.15 | 53.50 | 47.58 | 48.65 | 74.74 | 39.77 |
| | T24 | — | — | — | — | — | 8.76 | — | — | — | 10.50 | 63.41 | 4.91 | 8.76 | 6.51 | 56.17 | 8.21 | 5.96 | 5.54 | 58.66 | 5.62 |
| | UM-UC-3 | — | — | — | — | — | 11.12 | — | — | — | 22.07 | 36.00 | 20.91 | 12.29 | 27.58 | 22.86 | 18.08 | 25.76 | 21.01 | 25.44 | 21.67 |
| | H-bc | — | — | — | — | — | 72.55 | — | — | — | 73.72 | 73.03 | 35.05 | 81.70 | 36.08 | 78.21 | 75.08 | 15.01 | 3.23 | 76.61 | 4.30 |
| | ACS (%) | — | — | — | — | — | 23.03 | — | — | — | 24.88 | 35.93 | 15.26 | 26.23 | 16.16 | 36.43 | 23.49 | 13.93 | 12.20 | 37.52 | 13.60 |

TABLE 3

Further experimental testing of EH/Ci/Mi regimen (1). The combinations (1-34) vary with the dose (ng/mL) of three drugs and the cell survival (%) of each treated cell lines are measured for each of the ACS (%).

| | | Combinations | | | | | | | | |
|---|---|---|---|---|---|---|---|---|---|---|
| | | 1 | 2 | 3 | 4 | 5 | 6 | 7 | 8 | 9 |
| Drug concentration (ng/ml) | Pi | 0 | 0 | 0 | 40 | 0 | 0 | 0 | 8 | 0 |
| | Pa | 0 | 0 | 160 | 0 | 0 | 0 | 32 | 0 | 0 |
| | EH | 0 | 250 | 0 | 0 | 0 | 50 | 0 | 0 | 0 |
| | Ci | 1500 | 1500 | 1500 | 1500 | 1500 | 1500 | 1500 | 1500 | 1500 |
| | Ge | 0 | 0 | 0 | 0 | 5 | 0 | 0 | 0 | 1 |
| | Mi | 1000 | 1000 | 1000 | 1000 | 1000 | 1000 | 1000 | 1000 | 1000 |
| Cell survival (%) | Biu87 | 4.5 | 2 | 1.3 | 3.5 | 5.7 | 4.3 | 1.9 | 1.7 | 3.5 |
| | EJ | 17 | 15.4 | 10.4 | 16.7 | 20 | 22.4 | 14.3 | 20 | 19.4 |
| | H-bc | 29.5 | 4.79 | 19.82 | 5.84 | 7.57 | 5.11 | 42.68 | 8.5 | 29.95 |
| | T24 | 3.6 | 1.6 | 3.7 | 1.6 | 4.8 | 3.2 | 3.9 | 3.8 | 4.5 |
| | UM-UC-3 | 3 | 2.9 | 3 | 3.6 | 3.5 | 2.7 | 3 | 3.6 | 3.1 |
| | ACS (%) | 11.52 | 5.34 | 7.64 | 6.25 | 8.31 | 7.54 | 13.16 | 7.52 | 12.09 |

| | | Combinations | | | | | | | |
|---|---|---|---|---|---|---|---|---|---|
| | | 10 | 11 | 12 | 13 | 14 | 15 | 16 | 17 |
| Drug concentration (ng/ml) | Pi | 0 | 0 | 0 | 40 | 0 | 0 | 0 | 0 |
| | Pa | 0 | 0 | 160 | 0 | 0 | 0 | 0 | 160 |
| | EH | 0 | 250 | 0 | 0 | 0 | 0 | 250 | 0 |
| | Ci | 1500 | 1500 | 1500 | 1500 | 1500 | 300 | 300 | 300 |
| | Ge | 0 | 0 | 0 | 0 | 5 | 0 | 0 | 0 |
| | Mi | 200 | 200 | 200 | 200 | 200 | 1000 | 1000 | 1000 |
| Cell survival (%) | Biu87 | 5.3 | 0.6 | 1.9 | 2.8 | 3.7 | 13.4 | 9.9 | 10.7 |
| | EJ | 27.7 | 16.7 | 25.1 | 22.5 | 25.7 | 30.9 | 29.8 | 23.5 |
| | H-bc | 41.03 | 12.43 | 13.56 | 17.24 | 32.23 | 57.1 | 29.7 | 44 |
| | T24 | 5.6 | 6.5 | 1.6 | 3.5 | 8.9 | 7.09 | 29.5 | 7.69 |
| | UM-UC-3 | 4.6 | 3.6 | 4.2 | 4.1 | 4.1 | 32 | 14.1 | 19.4 |
| | ACS (%) | 16.85 | 7.97 | 9.27 | 10.03 | 14.93 | 28.10 | 22.60 | 21.06 |

| | | Combinations | | | | | | | | |
|---|---|---|---|---|---|---|---|---|---|---|
| | | 18 | 19 | 20 | 21 | 22 | 23 | 24 | 25 | 26 |
| Drug concentration (ng/ml) | Pi | 140 | 0 | 0 | 0 | 0 | 40 | 0 | 40 | 40 | 40 |
| | Pa | 0 | 0 | 0 | 0 | 160 | 0 | 0 | 32 | 0 | 0 |
| | EH | 0 | 0 | 0 | 250 | 0 | 0 | 0 | 0 | 50 | 0 |
| | Ci | 300 | 300 | 300 | 300 | 300 | 300 | 300 | 300 | 300 | 300 |
| | Ge | 0 | 5 | 0 | 0 | 0 | 0 | 5 | 0 | 0 | 1 |
| | Mi | 1000 | 1000 | 200 | 200 | 200 | 200 | 200 | 200 | 200 | 200 |
| Cell survival (%) | Biu87 | 13.3 | 6.8 | 36.4 | 21.7 | 27.2 | 30.7 | 8.4 | 30.4 | 29.3 |
| | EJ | 31.8 | 27 | 52.8 | 40.9 | 38.7 | 55.9 | 39.3 | 38.1 | 47.8 |
| | H-bc | 49.9 | 50.3 | 73.2 | 48.4 | 55.9 | 49.9 | 64.2 | 55 | 58.3 |
| | T24 | 12.76 | 71.7 | 8.87 | 45.97 | 55.81 | 46.27 | 50.98 | 40.97 | 34.88 |
| | UM-UC-3 | 25.5 | 34.6 | 64.5 | 30.1 | 32.3 | 22.1 | 49.6 | 37.1 | 30.9 |
| | ACS (%) | 26.65 | 38.08 | 47.15 | 37.41 | 41.98 | 40.97 | 42.50 | 40.31 | 40.24 |

| | | Combinations | | | | | | | |
|---|---|---|---|---|---|---|---|---|---|
| | | 27 | 28 | 29 | 30 | 31 | 32 | 33 | 34 |
| Drug concentration (ng/ml) | Pi | 140 | 8 | 0 | 0 | 0 | 8 | 0 | 0 | 40 |
| | Pa | 0 | 0 | 32 | 0 | 32 | 0 | 0 | 0 | 32 |
| | EH | 0 | 0 | 0 | 50 | 250 | 250 | 250 | 250 | 50 |
| | Ci | 300 | 300 | 300 | 300 | 300 | 300 | 300 | 300 | 1500 |
| | Ge | 0 | 5 | 5 | 5 | 0 | 0 | 1 | 5 | 5 |
| | Mi | 1000 | 200 | 200 | 200 | 200 | 200 | 200 | 200 | 200 |
| Cell survival (%) | Biu87 | 24.2 | 14.9 | 12.5 | 14.5 | 28.1 | 27.3 | 22.7 | 13.2 |
| | EJ | 48.4 | 46.5 | 37.5 | 44.9 | 40.5 | 45.1 | 49.9 | 40.4 |
| | H-bc | 70.9 | 63 | 63.1 | 58.6 | 47.8 | 33.1 | 45.4 | 51.9 |
| | T24 | 46.03 | 51.52 | 47.05 | 53.67 | 33.09 | 31.25 | 39.53 | 33.27 |
| | UM-UC-3 | 43.4 | 58.7 | 41.1 | 49.7 | 19.7 | 17.1 | 22.4 | 21.2 |
| | ACS (%) | 46.59 | 46.92 | 40.25 | 44.27 | 33.84 | 30.77 | 35.99 | 31.99 |

TABLE 4

The drug-triggered pathway activity of five cell lines of distinct chemoresistance. (A) The relative drug triggered pathway activities over the no-drug level of each cell line (fold) are listed, digitalized (B) and summarized (C). (D) The correlation coefficients of the collective drug-triggered pathway activities between each component drug versus EH/Ci/Mi regimen in each cell line are shown.

| | Drugs | | | | | | | | | | | | | | | | | | | |
|---|---|---|---|---|---|---|---|---|---|---|---|---|---|---|---|---|---|---|---|---|
| | Ci | | | | | Mi | | | | | EH | | | | | EH/Ci/Mi | | | | |
| | Cell lines | | | | | | | | | | | | | | | | | | | |
| | 5637 | Biu87 | Um-Uc-3 | H-bc | SV-HUC-1 | 5637 | Biu87 | Um-Uc-3 | H-bc | SV-HUC-1 | 5637 | Biu87 | Um-Uc-3 | H-bc | SV-HUC-1 | 5637 | Biu87 | Um-Uc-3 | H-bc | SV-HUC-1 |
| DNA Damage | 2.17 | 0.63 | 0.68 | 1.69 | 1.54 | 2.87 | 1.35 | 1.37 | 1.08 | 1.75 | 3.42 | 1.04 | 1.71 | 6.13 | 2.5 | 3.76 | 0.72 | 1.55 | 4.07 | 2.33 |
| Hypoxia | 1.64 | 1.32 | 0.66 | 0.39 | 1.19 | 3.31 | 3.56 | 0.73 | 0.58 | 2.08 | 2.27 | 2.26 | 1.18 | 1.72 | 1.74 | 2.42 | 5.31 | 0.92 | 0.84 | 1.66 |
| ER Stress | 1.82 | 0.83 | 0.83 | 0.82 | 1.12 | 3.2 | 1.65 | 1.34 | 1.97 | 1.51 | 3.26 | 1.66 | 1.48 | 1.38 | 2.93 | 3.67 | 2.24 | 0.81 | 1.16 | 1.52 |
| Heat Shock | 0.65 | 1.52 | 0.79 | 1.19 | 0.93 | 1.38 | 4.54 | 0.93 | 0.3 | 1.01 | 1.04 | 1.06 | 0.67 | 0.86 | 0.91 | 1.91 | 1.29 | 0.48 | 0.85 | 1.06 |
| Wnt | 1.14 | 0.41 | 0.48 | 0.78 | 1.25 | 1.87 | 1.06 | 1.13 | 0.55 | 1.29 | 1.19 | 0.95 | 1.15 | 1.03 | 1.05 | 1.39 | 0.61 | 0.81 | 1.21 | 1.21 |
| Notch | 1.39 | 0.5 | 1.01 | 0.31 | 1.44 | 2.2 | 1.45 | 1.5 | 0.42 | 0.95 | 1.92 | 1.34 | 2.05 | 1.6 | 1.3 | 3.67 | 1.7 | 1.51 | 0.79 | 1.19 |
| Cell Cycle/pRb-E2F | 1.95 | 0.55 | 0.39 | 0.51 | 1.71 | 2.64 | 1.46 | 0.37 | 0.3 | 1.39 | 5.15 | 3.95 | 2.91 | 1.47 | 2.45 | 3.8 | 0.79 | 1 | 1.09 | 1.43 |
| Myc/Max | 1.05 | 0.56 | 0.42 | 1.03 | 1 | 1.97 | 1.16 | 0.38 | 0.75 | 1.45 | 1.5 | 1.66 | 0.44 | 1.37 | 1.13 | 2.49 | 2.25 | 0.7 | 2.93 | 0.91 |
| MAPK/ERK | 1.74 | 0.66 | 0.51 | 0.71 | 1.65 | 3.73 | 2.04 | 1.06 | 0.45 | 1.42 | 2.26 | 1.24 | 1.29 | 0.75 | 0.95 | 2.96 | 1.09 | 0.77 | 0.77 | 1.02 |
| Negative control | 1 | 1 | 1 | 1 | 1 | 1 | 1 | 1 | 1 | 1 | 1 | 1 | 1 | 1 | 1 | 1 | 1 | 1 | 1 | 1 |
| Cell survival 72 hours | 2.23% | 12.93% | 9.33% | 1.61% | 26.21% | 35.46% | 21.74% | 54.71% | 81.16% | 91.17% | 2.23% | 23.24% | 25.19% | 2.60% | 61.89% | 1.06% | 12.50% | 4.20% | 0.48% | 47.47% |

| Pathway activity | 5637 | | | | Biu87 | | | | UM-UC-3 | | | | H-bc | | | | SV-HUC-1 | | | |
|---|---|---|---|---|---|---|---|---|---|---|---|---|---|---|---|---|---|---|---|---|
| | Ci | Mi | EH | Tri | Ci | Mi | EH | Tri | Ci | Mi | EH | Tri | Ci | Mi | EH | Tri | Ci | Mi | EH | Tri |
| DNA Damage | 1 | 1 | 1 | 1 | 0 | 1 | 0 | 0 | 0 | 1 | 1 | 0 | 1 | 0 | 1 | 1 | 1 | 1 | 1 | 1 |
| Hypoxia | 1 | 1 | 1 | 1 | 1 | 1 | 1 | 1 | 0 | 0 | 0 | 0 | 0 | 0 | 0 | 0 | 0 | 1 | 1 | 1 |
| ER Stress | 1 | 1 | 1 | 1 | 0 | 1 | 1 | 1 | 0 | 1 | 1 | 0 | 0 | 0 | 0 | 0 | 0 | 0 | 1 | 0 |
| Heat Shock | 0 | 1 | 0 | 1 | 1 | 1 | 1 | 1 | 0 | 0 | 0 | 0 | 1 | −1 | 0 | 0 | 0 | 0 | 0 | 0 |
| Wnt | 0 | 1 | 1 | 1 | 0 | 0 | 0 | 0 | 0 | 1 | 1 | 1 | 0 | 0 | 1 | 0 | −1 | 1 | 1 | 1 |
| Notch | 0 | 1 | 1 | 1 | 0 | 1 | 1 | 1 | 1 | 1 | 1 | 1 | −1 | 0 | 1 | 0 | −1 | 0 | 1 | 0 |
| Cell Cycle/pRb-E2F | 1 | 1 | 1 | 1 | 0 | 0 | 1 | 0 | 0 | 0 | 1 | 0 | 0 | −1 | 1 | 0 | 1 | 0 | 1 | 0 |
| Myc/Max | 0 | 1 | 1 | 1 | 0 | 0 | 1 | 1 | 0 | 0 | 1 | −1 | 0 | 0 | 0 | 0 | 0 | 0 | 1 | 0 |
| MAPK/ERK | 1 | 1 | 1 | 1 | −1 | 0 | 1 | 1 | 0 | 0 | 1 | −1 | 0 | −1 | 0 | 0 | 1 | 1 | 0 | 0 |
| ACS (%) | 2.23% | 35.46% | 2.23% | 1.06% | 12.93% | 21.74% | 23.24% | 12.50% | 9.33% | 54.71% | 25.19% | 4.20% | 1.61% | 81.16% | 2.60% | 0.48% | 26.21% | 91.17% | 61.89% | 47.47% |

TABLE 4-continued

The drug-triggered pathway activity of five cell lines of distinct chemoresistance. (A) The relative drug trigged pathway activities over the no-drug level of each cell line (fold) are listed, digitalized (B) and summarized (C). (D) The correlation coefficients of the collective drug-triggered pathway activities between each component drug versus EH/Ci/Mi regimen in each cell line are shown.

| Digitalized drug-triggered changes | 5637 | | | Biu87 | | | UM-UC-3 | | | H-bc | | | SV-HUC-1 | | |
|---|---|---|---|---|---|---|---|---|---|---|---|---|---|---|---|
| | (1) | 0 | (-1) | (1) | 0 | (-1) | (1) | 0 | (-1) | (1) | 0 | (-1) | (1) | 0 | (-1) |
| Ci | 5 | 3 | 1 | 1 | 6 | 2 | 6 | 0 | 3 | 1 | 5 | 3 | 3 | 6 | 0 |
| Mi | 8 | 1 | 0 | 4 | 5 | 0 | 2 | 5 | 2 | 1 | 3 | 5 | 3 | 6 | 0 |
| EH | 6 | 3 | 0 | 4 | 5 | 0 | 4 | 3 | 1 | 3 | 6 | 0 | 4 | 5 | 0 |
| EH/Ci/Mi | 8 | 1 | 0 | 4 | 4 | 1 | 2 | 6 | 1 | 2 | 7 | 0 | 3 | 6 | 0 |

| Correlation coefficients | 5637 | Biu87 | UmUc3 | H-bc | SV-HUC-1 |
|---|---|---|---|---|---|
| | | | EH/Ci/Mi | | |
| Ci | 0.917663 | 0.327327 | -0.75593 | 0.693375 | 1 |
| Mi | 1 | 0.981981 | 0.981981 | -0.27735 | 1 |
| EH | 0.917663 | 0.981981 | 0.371154 | 0.970725 | 0.944911 |

TABLE S1

Origin of cells and chemotherapy drugs

| Cell line | ATCC | Medium + 10% fetal serum (Invitrogen, USA) | Description |
|---|---|---|---|
| SV-HUC-1 | CRL-9520 ™ | Ham's F12 K(5) | Normal uroepithelium cell line |
| SCaBER | HTB-3 ™ | MEM | Squamous-cell carcinoma cell line |
| J82 | HTB-1 ™ | MEM | Muscle invasive transitional cell carcinoma line |
| UM-UC-3 | CRL-1749 ™ | MEM | Muscle invasive transitional cell carcinoma line |
| T24 | HTB-4 ™ | RPMI 1640 | Muscle invasive transitional cell carcinoma line |
| 5637 | HTB-9 ™ | RPMI 1640 | Muscle invasive transitional cell carcinoma line |
| EJ | Null | RPMI 1640 | Muscle invasive transitional cell carcinoma line, established by Marshall CJ in 1977 |
| H-bc | Null | RPMI 1640 | Muscle invasive transitional cell carcinoma line, established by cancer research Institute of Kunming Medical College, 1986 |
| Biu87 | Null | RPMI 1640 | Superficial bladder cancer, established by department of Urology of Beijing Medical University in 1987 |

TABLE S2

The $2^{nd}$ round of iteration. The combinations (1-20) vary with the dose (ng/mL) of six drugs and have different effects on the cell survival (%). The ACS (%) provides an overall measure of survival of all the cell lines in response to each combination.

| | | Combinations | | | | | | | | | |
|---|---|---|---|---|---|---|---|---|---|---|---|
| | | 1 | 2 | 3 | 4 | 5 | 6 | 7 | 8 | 9 | 10 |
| Drug concentration (ng/ml) | Pi | 8 | 0.32 | 40 | 0.32 | 8 | 8 | 1.6 | 8 | 40 | 0.32 |
| | Pa | 6.4 | 1.28 | 6.4 | 32 | 1.28 | 6.4 | 32 | 160 | 1.28 | 160 |
| | EH | 250 | 10 | 10 | 50 | 2 | 50 | 10 | 250 | 250 | 2 |
| | Ci | 12 | 1500 | 12 | 60 | 300 | 1500 | 1500 | 60 | 300 | 60 |
| | Ge | 0.04 | 0.04 | 1 | 0.04 | 5 | 1 | 5 | 1 | 0.2 | 1 |
| | Mi | 200 | 200 | 40 | 40 | 200 | 1000 | 200 | 8 | 40 | 200 |
| Cell survival (%) | 5637 | 41.90 | 33.17 | 65.54 | 54.93 | 34.82 | 16.36 | 38.54 | 51.28 | 52.93 | 36.99 |
| | H-bc | 76.86 | 75.17 | 73.66 | 75.43 | 75.43 | 67.23 | 73.62 | 78.67 | 76.38 | 74.87 |
| | Biu87 | 27.18 | 24.43 | 56.05 | 58.58 | 36.57 | 6.60 | 36.47 | 59.51 | 44.11 | 29.61 |
| | EJ | 35.64 | 39.25 | 41.01 | 53.31 | 42.50 | 31.07 | 39.52 | 52.48 | 37.93 | 28.92 |
| | J-82 | 44.07 | 36.94 | 54.84 | 73.33 | 40.23 | 20.95 | 45.53 | 50.92 | 55.05 | 40.77 |
| | T24 | 51.61 | 34.64 | 67.07 | 53.90 | 44.68 | 14.28 | 40.47 | 54.26 | 52.51 | 38.60 |
| | ACS (%) | 46.21 | 40.60 | 59.70 | 61.58 | 45.71 | 26.08 | 45.69 | 57.85 | 53.15 | 41.63 |
| Drug concentration (ng/ml) | Pi | 1.6 | 0.32 | 40 | 0.32 | 0.32 | 8 | 0.32 | 8 | 0.32 | 40 |
| | Pa | 6.4 | 160 | 32 | 6.4 | 6.4 | 6.4 | 6.4 | 6.4 | 1.28 | 1.28 |
| | EH | 10 | 10 | 50 | 2 | 10 | 50 | 10 | 0 | 250 | 250 |
| | Ci | 300 | 1500 | 60 | 1500 | 0 | 1500 | 12 | 1500 | 300 | 60 |
| | Ge | 0.2 | 0.2 | 1 | 1 | 5 | 0.2 | 0.2 | 5 | 5 | 0.04 |
| | Mi | 8 | 40 | 200 | 1000 | 1000 | 1000 | 200 | 40 | 40 | 8 |
| Cell survival (%) | Biu87 | 29.50 | 4.79 | 19.82 | 5.84 | 7.57 | 4.11 | 42.68 | 8.50 | 29.95 | 41.03 |
| | EJ | 64.82 | 38.64 | 38.32 | 43.59 | 59.47 | 36.31 | 53.72 | 51.39 | 52.79 | 65.94 |
| | J-82 | 53.51 | 1.41 | 9.69 | 0.05 | 6.01 | 0.19 | 22.28 | 3.47 | 19.35 | 28.05 |
| | T24 | 49.79 | 9.55 | 25.80 | 8.27 | 14.12 | 7.94 | 55.31 | 7.90 | 17.90 | 21.93 |
| | 5637 | 70.21 | 80.31 | 65.63 | 61.15 | 59.62 | 47.02 | 68.73 | 82.41 | 69.40 | 71.11 |
| | H-bc | 51.65 | 10.95 | 57.71 | 8.79 | 68.66 | 6.80 | 73.38 | 22.34 | 59.52 | 45.37 |
| | ACS (%) | 53.25 | 24.28 | 36.16 | 21.28 | 35.91 | 17.06 | 52.68 | 29.33 | 41.49 | 45.57 |

| | | Combinations | | | | | | | | | |
|---|---|---|---|---|---|---|---|---|---|---|---|
| | | 11 | 12 | 13 | 14 | 15 | 16 | 17 | 18 | 19 | 20 |
| Drug concentration (ng/ml) | Pi | 1.6 | 0.32 | 1.6 | 0.32 | 8 | 40 | 1.6 | 40 | 40 | 1.6 |
| | Pa | 1.28 | 32 | 1.28 | 6.4 | 6.4 | 160 | 160 | 160 | 32 | 32 |
| | EH | 10 | 50 | 50 | 250 | 10 | 50 | 250 | 2 | 2 | 2 |
| | Ci | 12 | 12 | 60 | 1500 | 300 | 300 | 300 | 1500 | 60 | 12 |
| | Ge | 0.2 | 5 | 5 | 1 | 0.04 | 5 | 0.2 | 0.2 | 0.04 | 0.2 |
| | Mi | 1000 | 1000 | 8 | 8 | 8 | 200 | 1000 | 40 | 1000 | 8 |
| Cell survival (%) | 5637 | 31.49 | 15.81 | 65.63 | 52.51 | 71.42 | 32.88 | 21.63 | 45.97 | 19.01 | 64.95 |
| | H-bc | 74.70 | 65.85 | 80.87 | 74.35 | 78.20 | 67.23 | 63.73 | 69.78 | 66.02 | 66.49 |
| | Biu87 | 12.43 | 10.97 | 71.59 | 44.66 | 65.15 | 25.21 | 7.61 | 32.88 | 8.19 | 56.60 |
| | EJ | 46.66 | 43.61 | 77.21 | 40.11 | 67.82 | 35.57 | 20.30 | 38.55 | 33.46 | 82.27 |
| | J-82 | 25.04 | 15.36 | 73.49 | 45.41 | 70.57 | 31.63 | 24.00 | 40.32 | 23.62 | 86.56 |
| | T24 | 22.32 | 15.67 | 75.85 | 46.27 | 69.44 | 34.97 | 16.44 | 40.72 | 23.79 | 51.16 |
| | ACS (%) | 35.44 | 27.88 | 74.11 | 50.55 | 70.43 | 37.92 | 25.62 | 44.70 | 29.01 | 68.01 |

TABLE S2-continued

The 2$^{nd}$ round of iteration. The combinations (1-20) vary with the dose (ng/mL) of six drugs and have different effects on the cell survival (%). The ACS (%) provides an overall measure of survival of all the cell lines in response to each combination.

| | | | | | | | | | | | |
|---|---|---|---|---|---|---|---|---|---|---|---|
| Drug concentration (ng/ml) | Pi | 1.6 | 0.32 | 0.32 | 40 | 40 | 40 | 0.32 | 8 | 1.6 | 1.6 |
| | Pa | 160 | 160 | 160 | 160 | 6.4 | 6.4 | 32 | 1.28 | 6.4 | 6.4 |
| | EH | 10 | 50 | 50 | 50 | 50 | 10 | 250 | 50 | 50 | 250 |
| | Ci | 12 | 60 | 0 | 12 | 1500 | 12 | 1500 | 1500 | 60 | 1500 |
| | Ge | 0.2 | 5 | 5 | 1 | 5 | 5 | 0.2 | 5 | 0.04 | 0.04 |
| | Mi | 1000 | 200 | 40 | 200 | 1000 | 200 | 1000 | 40 | 8 | 200 |
| Cell survival (%) | Biu87 | 13.56 | 12.43 | 17.24 | 32.23 | 7.09 | 29.50 | 7.69 | 12.76 | 71.70 | 8.87 |
| | EJ | 43.91 | 48.97 | 78.33 | 48.25 | 34.98 | 51.59 | 30.56 | 50.82 | 92.92 | 29.27 |
| | J-82 | 2.99 | 18.32 | 36.14 | 8.37 | 0.05 | 17.42 | 0.52 | 3.23 | 69.57 | 1.08 |
| | T24 | 15.88 | 20.25 | 31.85 | 31.98 | 8.60 | 26.34 | 10.41 | 9.75 | 86.21 | 9.84 |
| | 5637 | 50.83 | 54.02 | 61.87 | 57.74 | 41.50 | 63.21 | 26.51 | 74.52 | 75.37 | 62.85 |
| | H-bc | 43.16 | 63.29 | 71.34 | 57.27 | 2.25 | 69.48 | 0.52 | 15.02 | 94.07 | 1.52 |
| | ACS (%) | 28.39 | 36.21 | 49.46 | 39.31 | 15.75 | 42.92 | 12.70 | 27.68 | 81.64 | 18.91 |

TABLE S3

The 3$^{rd}$ round of iteration. The combinations (1-20) vary with the dose (ng/mL) of six drugs and have different effects on the cell survival (%). The ACS (%) provides an overall measure of survival of all the cell lines in response to each combination.

| | | Combinations | | | | | | | | |
|---|---|---|---|---|---|---|---|---|---|---|
| | | 1 | 2 | 3 | 4 | Pi | Pa | EH | Ci | Mi |
| Drug concentration (ng/ml) | Pi | 0 | 0 | 0 | 40 | 40 | 0 | 0 | 0 | 0 |
| | Pa | 0 | 0 | 160 | 0 | 0 | 160 | 0 | 0 | 0 |
| | EH | 0 | 250 | 0 | 0 | 0 | 0 | 250 | 0 | 0 |
| | Ci | 1500 | 1500 | 1500 | 1500 | 0 | 0 | 0 | 1500 | 0 |
| | Mi | 200 | 200 | 200 | 200 | 0 | 0 | 0 | 0 | 200 |
| Cell survival (%) | 5637 | 18.3 | 1.06 | 7.8 | 4.36 | 29.22 | 6.45 | 14.75 | 20.32 | 53.16 |
| | Biu87 | 13.7 | 12.5 | 8.5 | 12.3 | 41.67 | 23.08 | 38.68 | 20.94 | 42.05 |
| | J82 | 17.9 | 7.26 | 11.8 | 7.7 | 55.37 | 38.51 | 45.03 | 15.42 | 48.38 |
| | T24 | 15.5 | 5.82 | 6.73 | 10.4 | 48.33 | 11.55 | 20.13 | 15.46 | 51.34 |
| | EJ | 24.85 | 17.14 | 18.32 | 18.01 | 30.38 | 33.05 | 56.55 | 32.34 | 45.2 |
| | UM-UC-3 | 13.1 | 4.2 | 7.02 | 8.86 | 65.59 | 40.09 | 43.54 | 14.71 | 66.2 |
| | H-bc | 43.74 | 0.48 | 34.73 | 5.93 | 86.89 | 13.96 | 61.03 | 41.98 | 91.67 |
| | SCaBER | 17.63 | 3.01 | 14.22 | 3.49 | 30.04 | 57.91 | 38.31 | 22.05 | 56.83 |
| | ACS (%) | 20.59 | 6.43 | 13.64 | 8.88 | 48.44 | 28.08 | 39.75 | 22.9 | 56.85 |

TABLE S4

Further experimental testing of the EH/Ci/Mi regimen (1). The tri-drug combinations (1-4) and five drug at one fold dose (ng/mL) are indicated and the cell survival (%) of each treated cell lines are measured, from which the ACS (%) of each combination is calculated (A). The EH/Ci/Mi regimen and each of six drug at four fold dose (ng/mL) and the cell survival (%) of each treated cell lines (B) are measured, are indicated and the cell survival (%).

| Single drug 4X Cell Survival (%) | 5637 | Biu87 | T24 | EJ | UM-UC-3 | H-bc | SCaBER | ACS (%) for cancer cells | SV-HUC-1 |
|---|---|---|---|---|---|---|---|---|---|
| EH = 1000 (ng/ml) | 2.23 | 23.24 | 17.79 | 38.46 | 25.19 | 2.6 | 6.67 | 16.60 | 61.89 |
| Ci = 6000 (ng/ml) | 1.49 | 12.93 | 10.49 | 22.36 | 9.33 | 1.61 | 5.58 | 9.11 | 26.21 |
| Mi = 800 (ng/ml) | 35.46 | 21.74 | 19.72 | 28.67 | 54.74 | 81.16 | 41.97 | 40.49 | 91.17 |
| Pi = 160 (ng/ml) | 3.48 | 26.98 | 39.8 | 21.25 | 31.44 | 16.04 | 10.24 | 21.32 | 91.79 |
| Pa = 640 (ng/ml) | 2.09 | 17.58 | 17.31 | 26.38 | 27.74 | 12.89 | 42.21 | 20.89 | 80.17 |
| Ge = 20 (ng/ml) | 30.06 | 30.82 | 41.49 | 31.95 | 46.97 | 83.17 | 30.87 | 42.19 | 87.83 |
| EH/Ci/Mi | 1.06 | 12.5 | 5.82 | 17.14 | 4.2 | 0.48 | 3.01 | 6.32 | 47.47 |

TABLE S5

The signaling pathway analysis. The pathway analysis using the Qiagen pathway analysis kit in 5637 (A), Biu87 (B), UM-UC-3 (C), H-bc (D) and SV-HUC-1 (E). The transfection of cells was performed in duplicate. The cell lysate from two transfected cells the pair were combined for the activities of both firefly luciferase and renillagenes, which are listed as luc and Renluc in each treatment. Background relative luciferase activities were listedas Mock. Luciferase activities of the EH/Ci/Mi combination versus that by 4 folds of the single drug: Ci, Mi, EH were listed in tables.

| | Mock | | | Ci | | | Mi | | | EH | | | EH/Ci/Mi | | |
|---|---|---|---|---|---|---|---|---|---|---|---|---|---|---|---|
| | luc | Renluc | Relative activity | luc | Renluc | Relative activity | luc | Renluc | Relative activity | luc | Renluc | Relative activity | luc | Renluc | Relative activity |
| 5637 | | | | | | | | | | | | | | | |
| DNA Damage | 12536 | 29072830 | 0.22 | 16463 | 30579432 | 0.48 | 17956 | 34938044 | 0.63 | 16120 | 30098156 | 0.75 | 15629 | 26196576 | 0.83 |
| Hypoxia | 1052057 | 23600716 | 22.72 | 1024324 | 24274040 | 37.36 | 1352097 | 22097140 | 75.18 | 808185 | 22038922 | 51.46 | 906153 | 22826258 | 54.96 |
| ER Stress | 1601415 | 21382872 | 26.01 | 1662012 | 31011830 | 47.45 | 2175983 | 32174418 | 83.09 | 1698175 | 28112488 | 84.76 | 2088434 | 30298250 | 95.44 |
| Heat Shock | 511659 | 18502666 | 14.09 | 256314 | 24711858 | 9.18 | 423550 | 26726118 | 19.47 | 241002 | 23164298 | 14.60 | 433669 | 23347410 | 26.87 |
| Wnt | 47316 | 27569552 | 0.87 | 29940 | 26540942 | 1.00 | 36165 | 27194420 | 1.63 | 19535 | 26427688 | 1.04 | 20032 | 22864232 | 1.21 |
| Notch | 42575 | 21358194 | 1.02 | 36939 | 23115178 | 1.41 | 46653 | 25672570 | 2.23 | 36211 | 25995968 | 1.95 | 55387 | 20590916 | 3.72 |
| Cell Cycle/pRb-E2F | 90588 | 50884692 | 0.91 | 118387 | 59247780 | 1.77 | 122055 | 62526588 | 2.40 | 214150 | 64347208 | 4.67 | 141777 | 56925468 | 3.45 |
| Myc/Max | 634048 | 29187098 | 11.07 | 368299 | 28010318 | 11.64 | 475193 | 26813652 | 21.77 | 318258 | 26899256 | 16.61 | 479680 | 24095642 | 27.56 |
| MAPK/ERK | 2257440 | 22080312 | 52.10 | 2070782 | 20198954 | 90.77 | 2811788 | 17753446 | 194.59 | 1226693 | 14625057 | 117.70 | 1764958 | 15854674 | 154.13 |
| Negative control | 46553 | 23724400 | 1 | 29773 | 26360576 | 1 | 19188 | 23574666 | 1 | 14253 | 20000002 | 1 | 15134 | 20953624 | 1 |
| Positive control | 2827637 | 17096506 | 84.29 | 3033778 | 13923928 | 192.91 | 2465498 | 16347385 | 185.30 | 1537250 | 12755471 | 169.11 | 2013196 | 15850561 | 175.85 |
| Biu87 | | | | | | | | | | | | | | | |
| DNA Damage | 1170 | 2227384 | 1.51 | 1663 | 3531196 | 0.94 | 2890 | 5710684 | 2.03 | 1470 | 2834282 | 1.58 | 1371 | 5077079 | 1.08 |
| Hypoxia | 4451 | 1687236 | 7.58 | 7487 | 1499278 | 10.01 | 7691 | 1144978 | 26.99 | 6519 | 1156255 | 17.13 | 9376 | 936424 | 40.22 |
| ER Stress | 40626 | 5327666 | 21.92 | 74981 | 8302932 | 18.10 | 44361 | 4931940 | 36.14 | 52055 | 4349360 | 36.36 | 57183 | 4678703 | 49.10 |
| Heat Shock | 3389 | 5145078 | 1.89 | 9053 | 6321098 | 2.87 | 8222 | 3842602 | 8.60 | 3274 | 4953542 | 2.01 | 2263 | 3712893 | 2.45 |
| Wnt | 1084 | 1873321 | 1.66 | 1035 | 3005559 | 0.69 | 1100 | 2497907 | 1.77 | 1274 | 2458774 | 1.57 | 852 | 3350532 | 1.02 |
| Notch | 3188 | 2067691 | 4.43 | 4447 | 3994370 | 2.23 | 4045 | 2530636 | 6.42 | 4323 | 2210120 | 5.94 | 5131 | 2737670 | 7.53 |
| Cell Cycle/pRb-E2F | 1048 | 5308695 | 0.57 | 827 | 5334082 | 0.31 | 792 | 3836588 | 0.83 | 3978 | 5391695 | 2.24 | 751 | 6701679 | 0.45 |
| Myc/Max | 6849 | 2405994 | 8.18 | 10012 | 4361355 | 4.60 | 9217 | 3901945 | 9.49 | 13337 | 2976075 | 13.61 | 14966 | 3270559 | 18.38 |
| MAPK/ERK | 219738 | 1289376 | 489.80 | 223810 | 1396421 | 321.19 | 454932 | 1824789 | 1001.57 | 402732 | 2011157 | 608.33 | 210769 | 1578983 | 536.23 |
| Negative control | 2475 | 7113303 | 1 | 3696 | 7406714 | 1 | 2398 | 9633820 | 1 | 2575 | 7822520 | 1 | 2087 | 8383868 | 1 |
| Positive control | 111213 | 1913179 | 167.07 | 137362 | 1480354 | 185.95 | 123326 | 1627869 | 304.36 | 156600 | 1862408 | 255.44 | 194031 | 1520161 | 512.75 |
| UM-UC-3 | | | | | | | | | | | | | | | |
| DNA Damage | 5855 | 1472476 | 3.49 | 5325 | 2147032 | 2.38 | 8237 | 1502130 | 4.77 | 9467 | 1431776 | 5.96 | 8320 | 1524256 | 5.42 |
| Hypoxia | 33444 | 468141 | 62.72 | 25797 | 594608 | 41.68 | 29511 | 558774 | 45.95 | 39411 | 480634 | 73.93 | 29518 | 506501 | 57.87 |
| ER Stress | 91342 | 982640 | 81.61 | 71599 | 1019011 | 67.50 | 81715 | 648793 | 109.59 | 114029 | 849848 | 120.98 | 63215 | 948602 | 66.17 |
| Heat Shock | 929 | 187527 | 4.35 | 550 | 154516 | 3.42 | 1002 | 216089 | 4.03 | 536 | 164788 | 2.93 | 338 | 160863 | 2.09 |
| Wnt | 2272 | 555610 | 3.59 | 1099 | 610446 | 1.73 | 2244 | 480824 | 4.06 | 2599 | 568504 | 4.12 | 1253 | 430152 | 2.89 |
| Notch | 23352 | 4144667 | 4.95 | 20903 | 4021789 | 4.99 | 22993 | 2702600 | 7.40 | 34486 | 3060547 | 10.16 | 26857 | 3559553 | 7.49 |
| Cell Cycle/pRb-E2F | 1230 | 181856 | 5.94 | 561 | 234963 | 2.29 | 787 | 315046 | 2.17 | 3739 | 195419 | 17.25 | 1292 | 215829 | 5.94 |
| Myc/Max | 21009 | 316030 | 58.37 | 11423 | 449464 | 24.42 | 11805 | 458417 | 22.41 | 15832 | 560204 | 25.48 | 12508 | 303171 | 40.97 |

TABLE S5-continued

The signaling pathway analysis. The pathway analysis using the Qiagen pathway analysis kit in 5637 (A), Biu87 (B), UM-UC-3 (C), H-bc (D) and SV-HUC-1 (E). The transfection of cells were combined for the activities of both firefly luciferase and renillagenes, which are listed as luc and Renluc in each treatment. Background relative luciferase activities were listedas Mock. Luciferase activities of the EH/Ci/Mi combination versus that by 4 folds of the single drug: Ci, Mi, EH were listed in tables.

| | Mock | | | Ci | | | Mi | | | EH | | | EH/Ci/Mi | | |
|---|---|---|---|---|---|---|---|---|---|---|---|---|---|---|---|
| | luc | Renluc | Relative activity | luc | Renluc | Relative activity | luc | Renluc | Relative activity | luc | Renluc | Relative activity | luc | Renluc | Relative activity |
| MAPK/ERK | 93465 | 576801 | 142.27 | 54365 | 724900 | 72.05 | 96470 | 554587 | 151.35 | 134413 | 661484 | 183.22 | 70680 | 644165 | 108.95 |
| Negative control | 11172 | 9808636 | 1 | 10236 | 9833868 | 1 | 10178 | 8855745 | 1 | 10475 | 9444867 | 1 | 9389 | 9322670 | 1 |
| Positive control H-bc | 309127 | 2534228 | 107.09 | 266403 | 2002668 | 127.80 | 219764 | 2347988 | 81.44 | 328077 | 2808991 | 105.31 | 319831 | 2468161 | 128.67 |
| DNA Damage | 2015 | 3432545 | 0.80 | 1546 | 1281912 | 4.19 | 1185 | 1990956 | 0.73 | 2158 | 692083 | 3.99 | 2227 | 1073909 | 1.47 |
| Hypoxia | 93683 | 3105480 | 41.20 | 106095 | 7500511 | 49.11 | 108144 | 6568317 | 20.08 | 128282 | 2852609 | 57.60 | 151139 | 6899389 | 15.49 |
| ER Stress | 94542 | 4743843 | 27.22 | 163717 | 5594167 | 101.61 | 239204 | 6560323 | 44.48 | 181107 | 8106904 | 28.61 | 223897 | 10687862 | 14.81 |
| Heat Shock | 4692 | 1440244 | 4.45 | 8865 | 1886689 | 16.31 | 4846 | 5282890 | 1.12 | 4438 | 1818590 | 3.13 | 4225 | 1753539 | 1.70 |
| Wnt | 4284 | 4474023 | 1.31 | 5450 | 6023579 | 3.14 | 5492 | 11151935 | 0.60 | 7571 | 8824576 | 1.10 | 6611 | 6578338 | 0.71 |
| Notch | 1607 | 1298732 | 1.69 | 2219 | 4825030 | 1.60 | 1832 | 3790065 | 0.59 | 2986 | 1741009 | 2.20 | 2697 | 3162138 | 0.60 |
| Cell Cycle/pRb-E2F | 10459 | 3833178 | 3.73 | 11455 | 6792549 | 5.86 | 12829 | 17003119 | 0.92 | 17368 | 5010011 | 4.44 | 12065 | 4671758 | 1.83 |
| Myc/Max | 89185 | 7885777 | 15.85 | 120068 | 8299990 | 50.23 | 86926 | 10750527 | 9.86 | 92499 | 6723079 | 17.62 | 86003 | 2918818 | 20.84 |
| MAPK/ERK | 239072 | 2086866 | 156.44 | 290167 | 2958210 | 340.57 | 325601 | 6723697 | 59.07 | 331906 | 4467438 | 95.16 | 393552 | 5160822 | 53.92 |
| Negative control | 703 | 959998 | 1 | 954 | 3312384 | 1 | 914 | 1114948 | 1 | 838 | 1073349 | 1 | 724 | 511956 | 1 |
| Positive control SV-HUC-1 | 22609 | 2499255 | 12.35 | 14602 | 2857566 | 17.74 | 18615 | 6370362 | 3.56 | 13915 | 2479590 | 7.19 | 20173 | 1489971 | 9.57 |
| DNA Damage | 65065 | 26021553 | 2.40 | 67503 | 24632906 | 3.70 | 281508 | 31469814 | 4.20 | 310089 | 31955895 | 6.00 | 389590 | 26547677 | 5.60 |
| Hypoxia | 556794 | 21123753 | 25.30 | 437361 | 19553671 | 30.20 | 2225553 | 19903601 | 52.50 | 1665093 | 23399224 | 44.00 | 2546002 | 23132188 | 42.00 |
| ER Stress | 2999614 | 28089149 | 102.50 | 2127729 | 24981219 | 115.00 | 9579549 | 28980528 | 155.20 | 14481584 | 29847666 | 300.00 | 12552116 | 30704324 | 156.00 |
| Heat Shock | 683248 | 16560758 | 39.60 | 542556 | 19906350 | 36.80 | 2050872 | 24073070 | 40.00 | 1431915 | 24594061 | 36.00 | 2492592 | 22646922 | 42.00 |
| Wnt | 31879 | 24676048 | 1.24 | 24544 | 21379748 | 1.55 | 83472 | 24494884 | 1.60 | 58993 | 28058876 | 1.30 | 91080 | 23170671 | 1.50 |
| Notch | 85641 | 19116590 | 4.30 | 85503 | 18620163 | 6.20 | 201928 | 23124105 | 4.10 | 249971 | 27600509 | 5.60 | 278882 | 20866887 | 5.10 |
| Cell Cycle/pRb-E2F | 232505 | 45544197 | 4.90 | 296922 | 47726361 | 8.40 | 815673 | 56319698 | 6.80 | 1325887 | 68318891 | 12.00 | 1058228 | 57688414 | 7.00 |
| Myc/Max | 2999310 | 26123828 | 110.20 | 1833224 | 22563387 | 109.70 | 8230355 | 24151914 | 160.00 | 5773588 | 28559550 | 125.00 | 6399018 | 24418585 | 100.00 |
| MAPK/ERK | 4857155 | 19762919 | 235.90 | 4687804 | 16271033 | 389.00 | 11409592 | 15991097 | 335.00 | 5650354 | 15527755 | 225.00 | 10105164 | 16067167 | 240.00 |
| Negative control | 22123 | 21234456 | 1.00 | 15727 | 21234456 | 1.00 | 45226 | 21234456 | 1.00 | 34342 | 21234456 | 1.00 | 55646 | 21234456 | 1.00 |
| Positive control | 1992811 | 15302179 | 125.00 | 1287610 | 11216259 | 155.00 | 6679909 | 14724613 | 213.00 | 3854825 | 13542773 | 176.00 | 7450625 | 16062999 | 177.00 |

The In Vivo Study.

Cells ($1\times10^{6-7th}$/100 μL) embedded in BD Matrigel™ Matrix were subcutaneously injected at three sites in the back of each mouse (3-4 mice per treatment). On day 7-12$^{th}$ following cell injection, the animals were treated with the different drugs by an intraperitoneal injection, which was repeated every three days. Tumor volumes were monitored/calculated using the equation V=W$^2$L×0.5 (where W and L represent the largest and second largest tumor diameters (mm)) and then plotted. The tumor mass mice were weighed, fixed/sliced for immunohistochemistry after sacrificing the animals.

Immunohistochemistry Analysis.

Immunostaining was performed on 5 μm slices of formalin fixed paraffin-embedded tumor xenografts using antibodies from Gene Tech Company (Shanghai, China) against both Ki67 and CD34. Pictures were taken by LEICA DM 4000B microscope and the relative level of each protein was calculated using LEICA software. The relative staining per antibody (in percentage) in the mock treated over chemotherapeutic treated tumors was calculated and plotted.

Statistical Analysis.

Two sets of tumor xenograft/nude mice studies were carried out. The in vivo study involves 4 three mice each groups. Both mean±S.D of tumor volume and mass were calculated. Student's t-test was used for statistical comparisons. P values less than 0.05 were considered statistically significant.

Results

Bladder Cancer Cell Lines Vary Considerably in their Chemoresistance Properties

This example used the MTT based assay to determine the dose required for 50% cells to be killed (IC$_{50}$) by following six anti-bladder cancer drugs: Pirarubicin (Pi), Paclitaxel (Pa), Epirubicin Hydrochloride (EH), Cisplatin (Ci), Gemcitabine (Ge) and Mitomycin (Mi) in eight human bladder cancer cell lines (7 TCC lines: T24, Biu87, EJ, J82, UM-UC-3, 5637, H-bc) and one squamous carcinoma cell lines (SCaBER) and an immortalized benign cell line (SV-HUC-1) (FIG. 2A-F). The relative IC$_{50}$ (fold) of each drug of all nine cell lines was normalized to the lowest IC$_{50}$ in the most sensitive cell line (FIG. 2G), to describe the single drug resistance of cell lines. The overall chemoresistance of each cell line, a "chemoresistance index" (the numerator of the total relative IC$_{50}$ over the number of drugs) (FIG. 2G) were calculated to rank the overall resistance state of each cell line to this six chemotherapeutics. The results from the IC$_{50}$ profiling of these nine cell lines (FIG. 1) illustrate the considerable heterogeneity in drug resistance among BCa cell lines, despite an exception: a uniform sensitivity of all cell lines to Cisplatin. 5637 exhibits the highest chemo-sensitivity to four of six drugs and overall chemo-sensitivity for all six drugs ("chemoresistance" index: 1.62). H-bc was the most chemoresistant to three of six drugs, with an exceedingly high relative IC$_{50}$ to GE (3976.1), which makes it the most chemoresistant (the "chemoresistance" index: 678.68). It was the second highest in cancer cell line ("chemoresistance" index: 19.2) when GE was taken out from the consideration (FIG. 2G), to SCaBER ("chemoresistance index": 33.88). SV-HUC-1, an immortalized benign epithelial cell line exhibited the highest IC$_{50}$ to each of these five drugs and therefore a highest chemoresistance index: 147.28, which was almost 3.5 fold higher than SCaBER's (FIG. 2G). Therefore, these five drugs had a high level of cancer cell selective killing capability.

Identification of an Effective Tri-Drug Combination by the Differential Evolution (DE) Algorithm Guided Experimental Screening (the FSC Platform)

The total number of possible combinations for six drugs at five doses is 15,625 for one cell line and 125,000 for all eight BCa cell lines. This represents a prohibitive scale of workload if all potential combinations are examined. To experimentally identify an effective tri-drug combination in this study, the DE algorithm version of FSC platform was implemented. The FSC platform consisted of 4 iterative operations: 1) Starting with a randomly selected drug-dose combination, 2) Experimental assessment of combination-mediated cell killing efficacy, 3) Optimization of the combinations via DE algorithm, and 4) Completion of the feedback control loop by testing the newly selected drug-dose combination until an optimum is reached (FIG. 3).

Twenty six-drug combinations at the indicated doses were initially generated through a random number generator (using MATLAB MathWorks©, Natick, Mass., U.S.) (The upper half of Table 1). The cell survival (% over the not drug control) of treated cells was determined and then used for a calculation of the average cumulative cell survival (%, ACS: the sum of cell survival (%) per combination divided by the number of cell lines tested). ACS<30% was used to separate the effective from the not-effective combinations. Nine of the twenty combinations tested in the 1$^{st}$ round of iteration fell into this category (the lower half of Table 1).

The ACS of each combination of the 1$^{st}$ round testing was fed into a DE algorithm scheme to generate a new list of combinations for the next round of testing. Four (4) of the 20 six-drug combinations tested in the 2$^{nd}$ round of iteration were effective (Table S2). To reduce the number of drugs in combinations from six to four or five, a zero dose option was introduced in the 3$^{rd}$ and the 4$^{th}$ round of testing for four or five drug combinations. The number of the effective combinations rinsed from the 2$^{nd}$ round (25%, 4 out of 20) (Table S2) to the 3$^{rd}$ round (45%, 9 of 20) (Table S3), and the 4$^{th}$ round (82.5%, 33 out of 40) of testing (Table 2), demonstrating improved optimization with the "evolution" of drug combinations. More specifically, combination #40 (EH 250 ng/mL, highest dose; Ci 1500 ng/mL highest dose; Mi 200 ng/mL at the second highest dose; Pi at the lowest dose, 0.32 ng/mL) gave rise to the lowest ACS (13.60%) (Table 2). Pi, in this combination was at the lowest concentration and did not have any apparent impact on maintaining the efficient cell killing abilities of this regimen, suggested by a comparative analysis with other Pi inclusive combinations (Table 1-2, Table S2-3). Therefore, this example removed Pi and selected the combination 40 minus Pi (EH/Ci/Mi) as the candidate combination for the further refinement.

Statistical Modeling Analysis Confirmed EH/Ci/M as the Optimal Tri-Drug Combination For an additional support, this example performed statistical modeling analysis of all the features of the 100 combinations (Table 1-2 and S1-2) from testing of the following four cell lines: 5637 (sensitive), H-bc and UM-UC-3 (resistant) and the moderately resistant cell lines: Biu87 (FIG. 3).

For a given cancer cell line treated by six (k) different drugs (Pi, Pa, EH, Ci, Ge and Mi), the system output, y, can be expressed by a 2$^{nd}$ order polynomial regression model of drug doses $x_i$. The data confirm that higher than 2$^{nd}$ order terms do not make significant contributions to the efficacy, as was previously demonstrated in a lung cancer model.

$$y=\beta_0+\sum_{i=1}^{k}\beta_i x_i+\sum_{i=1}^{k}\beta_{ii}x_i^2+\sum_{i=1}^{k}\sum_{j=i+1}^{k}\beta_{ij}x_i x_j+\varepsilon \quad (1)$$

where $\beta_0$, $\beta_i$, $\beta_{ii}$ and $\beta_{ij}$ are the intercept, linear, quadratic and bilinear (or interaction) terms. The "observed" values represent the experimental data (ACS) and the "fitted" results represent the model predictions for the same drug combinations. A $2^{nd}$ order polynomial regression model fits the experimental results of Biu87, 5637, UM-UC-3 and H-bc which are plotted for comparison (FIG. 3).

This example further examined the regression coefficients in the statistical modeling for each of these four cell lines. For instance, the polynomial regression model for Biu87 is:

$$Biu87 ACS = 52.7 + 2\text{sixteen} \cdot 45 \times Pi - 31.37 \times Pa + 19.8 \times EH - 20.6 \times Ci - 3367.7 \times Ge - 110.8 \times Mi + 78364 \times Ge^2 + 65.6 \times Mi^2 - 2848 \times Pi \times EH + 19.3 \times Ci \times Mi + 2106 \times Ge \times Mi \quad (2)$$

where Biu87 ACS represents the ACS for Biu87 cells under different drug treatments. Pi, Pa, EH, Ci, Ge and Mi in the equation represent the absolute dosages of each drug (ng/mL). The model had a $R^2$ value of 0.7015 and p-value equals to $2.439e^{-15}$, which indicates a good fit between the model and experimental observations. The chemotherapeutic agent Ge had a negative linear regression coefficient but the largest positive quadratic regression coefficient. This implies that a dose increase of Ge is less likely to enhance drug-triggered cell death when it was used in combination with other drugs. Ge also had the largest positive two-drug interaction coefficient with Mi, implying that Ge and Mi would had antagonistic effects in reducing cell survival. Therefore, this example eliminated Ge for the further consideration.

The regression model for H-bc cell line is:

$$HbcACS = 64 - 9.3 \times Ci + 6.4 \times Mi - 29.5 \times Ci \times Mi \quad (3)$$

For H-bc cell line, only Ci and Mi were left in the final regression model and the rest of the drugs did not appear in the model. This equation showed that Ci and Mi were the most potent cytotoxic drugs for H-bc, which was resistant to other drugs. The interaction coefficient of $C_i \times M_i$ was negative, suggesting a synergistic cytotoxic effect of these two drugs on the H-bc cell line.

In summary, the statistical modeling analysis supports the conclusion that EH/Ci/Mi regimen is an optimized regimen suggested by testing 100 of 15,625 possible combination for a single cell line via DE algorithm guided experimental testing is supported.

Figure 4A:
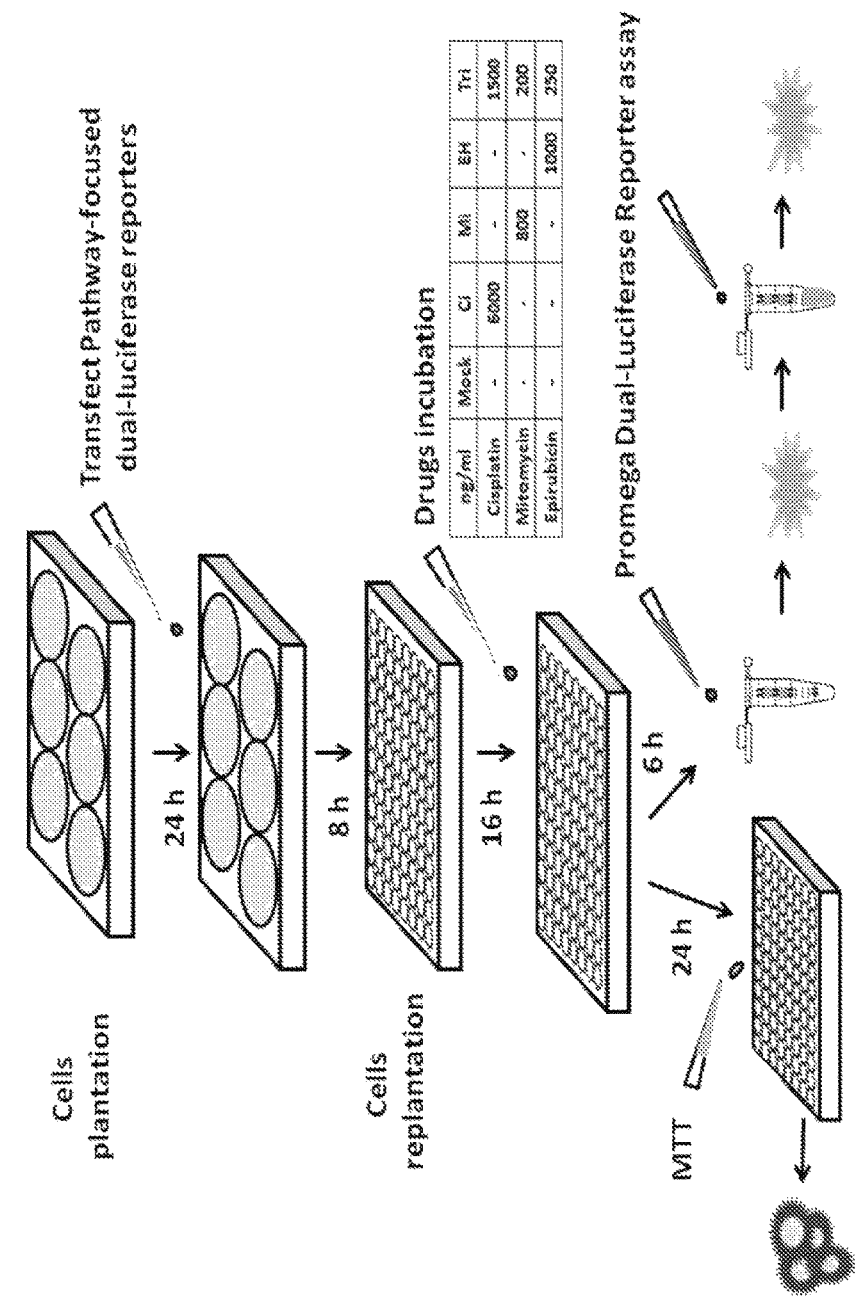

The EH/Ci/Mi Regimen More Effectively and Selectively Kills Cancer Cell Line than the Fold Dosed Component Drugs For further confirmation, the ACS of 34 combinations where both Ci and Mi were fixed at one of the two doses (Ci=1500 and Mi=1000 ng/mL), or the second highest doses (Ci=300 and Mi=200 ng/mL) alone or with one of a third drug at one of the three doses (the upper half of Table 3) were determined in the following TCC cell lines: Biu87, T24, 5637, UM-UC-3 and H-bc. Again, EH/Ci/Mi regimen (1500 ng/mL Ci, 200 ng/mL Mi and 250 ng/mL EH,) showed the lowest ACS value (7.97%) among all of the four tri-drug regimens (combinations 11-14) which was finally examined in all eight BCa cell lines (Table S3). The EH/Ci/Mi regimen (ACS: 6.32%, Table S4) not only delivered more cell killing than other tri-drug regimens, but was also more effective than the four-fold dosed component drugs: Ci (6000 ng/mL, ACS: 16.60%), Mi (800 ng/mL, ACS: 40.49%) or EH (1000 ng/mL, ACS: 9.11%), respectively. This observation suggests a synergistic action of the three drugs when they are used in combination. Furthermore, EH/Ci/Mi regimen possessed both a broad spectrum of anti-bladder cancer activity, by killing between 82.86% and 99.52% BCa cells in comparison to only 47.47% SV-HUC-1 cells died (Table S4). The Basal and Drug-Triggered Levels of Nine Cancer-Associated Signaling Pathway Activities Underlie the BCa Chemoresistance and EH/Ci/Mi Regimen's Broad Spectrum of Anti-Cancer Cell Capability The signaling pathway(s) impacted by conventional chemotherapeutic agents remain enigmatic, despite years of research effort. To provide the signaling pathway based mechanisms for BCa chemoresistance, this example used a Signal Pathway Finder reporter system (Qiagen) (FIG. 4A-C) to determine, in 5637 (chemo-sensitive), Biu87 (moderately resistant), UM-UC-3 and H-bc (resistant) BCa cell lines and SV-HUC-1 cell lines, the activities of the following nine signaling pathways that are known to be involved with cell survival and death of both healthy and disease cells: DNA Damage response, Hypoxia, ER Stress, Heat Shock, Wnt, Notch, Cell Cycle/pRb-E2F, Myc/Max, and MAPK/ERK pathways and normalized (Table S5), The relative pathway activity between more resistant cell lines: Biu87, Um-Uc-3, H-bc and SV-HUC-1 over the most chemo-sensitive cell line, 5637 was determined and analyzed (FIG. 4D). Eight pathways exhibit higher activities in Biu87 and SV-HUC-1 than in 5637 and 7 pathways show higher activity in UM-UC-3 and H-bc cells than 5637, by more than 0.5 fold. Therefore, a higher level of the basal activity of most pathways tested here is positively correlated with the chemoresistant state of BCa cells.

This example then determined the correlation coefficient between the overall activity of these nine pathways and the chemoresistance state of these five cell lines. The pathway activity was digitized as follows: (1) an active state: the signaling pathway with an activity higher by 0.5 fold than in 5637; (−1) an inactive state: the signaling pathway with an activity lower by 0.5 fold than 5637; and (0) an inert state: the signaling pathway with an activity being neither of the above. The overall state of activity of these pathways in each cell line are summarized (FIG. 4E) and the correlation coefficient of each pair of cell lines is calculated (FIG. 4F).

The correlation coefficients of the overall nine pathway activity between in 5637 and in four chemoresistant cell lines were negative (−0.397, −0.5, −0.5 and −0.397), indicating the distinct state of 5637 from the rest four cell lines, these figures in each pair were close to 0.99 (FIG. 4F). It was anticipated that the drug-triggered pathway activities also reflect the extent of chemoresistance of the cells. Cells were subjected to a 6 hrs treatment with either the EH/Ci/Mi regimen (EH, 250 ng/mL, Ci, 1500 ng/mL and Mi, 200 ng/mL) or each four-fold dosed: EH (1000 ng/mL), Ci (6000 ng/mL) and Mi (800 ng/mL) as well as two other drugs, respectively. EH/Ci/Mi regimen's ACS for BCa cells was significantly lower than that of any 4 fold dosed component drugs (and other two drugs), while was higher than a fold dosed Ci for SV-HUC-1 cells than 4 fold dosed Ci (Table S4). The 6 hrs post-drug-triggered pathway activities were measured (Table S5), normalized with the basal level activities (Table 4A), then digitalized (Table 4B) and summarized (Table 4C) for the correlation analysis of pathway activities by each single drug treatment and EH/Ci/Mi regimen (Table 4D). Taking 0.917 as the cutoff, EH/Ci/Mi regime's effect on the pathway activity same as that of all the three component drugs in 5637 cells. On the contrary, only one component drug (Mi, in UM-UC-3, EH, in H-bc) or two drugs (Mi and EH, in Biu87) triggered pathway activity were same as the EH/Ci/Mi regimen's. This observation suggests that the ability of EH/Ci/Mi regimen to evoke the pathway response by one or more 4 fold dosed single drugs may form the mechanistic basis for its a broad spectrum of cancer cell killing. Although the analysis of this level groups 5637 and SV-HUC-1 (the most resistant) cells together, the detailed difference is obvious. The number of drug-activated pathways was from 5-8 in 5637 in comparison 3-4 in SV-HUC-1 cells, while the number of the inert pathways to drug treatment in 5637 is 1 to 3 versus 5-6 in SV-HUC-1 cells (Table 4B and C).

EH/Ci/Mi Regimen Inhibited the In Vivo Growth of Bladder Cancer Cell Line Derived Tumor Xenografts in Nude Mice More Effectively than its Mono-Drug or Bi-Drug Counterparts This example then compared the in vivo anticancer activity of EH/Ci/Mi regimen with its mono- and bi-drug counterparts on the 5637, UM-UC-3, or Biu87 cells derived tumor xenografts in nude mice. Since there is no established conversion rule for the drug dose in cell culture to in nude mice, this example used 75 μg per mouse for the mono-drug treatments and 25 μg per drug per mouse for both bi-drug and tri-drug combinations, based on the maximum tolerated drug dose recommended for these drugs. To minimize the inter-mouse bias's effect on tumor growth, three different BCa cell line-derived tumor xenografts were individually established subcutaneously on the back of the twelve mice (FIG. 5A). A group of three mice were intraperitoneally, respectively, injected with PBS (the no-drug control), Ci, Ci/Mi and EH/Ci/Mi regimen on day 7 (after injection of the cancer cell lines) and at a three-day interval for four more times. The tumor volumes were measured once every three days and were normalized by the volume on day 7. As shown in FIG. 5B-F, the increase in tumor volume on day $28^{th}$ was 21 and 6.20 in PBS respectively for UM-UC-3 and Biu87, 10.58 and 4.95 in Ci, 8.87 and 4.37 in Ci/Mi treated, 2.25 and 2.54 in EH/Ci/Mi treatment mice (FIG. 5B). The relative tumor volume of 5637 cells in EH/Ci/Mi group (2.54) was lower than that in Ci (6.2) and Ci/Mi groups (4.95) (FIG. 5B). The conclusion of the better anti-cancer effect of EH/Ci/Mi than Ci and Ci/Mi regimen has further been supported by the different tumor masses on day $28^{th}$ when the animal study ended. Taken the tri-drug group as 1, relative tumor weight in the PBS group was 5.85, 1.14 and 1.84 for UM-UC-3, 5637 and Biu87 derived tumor, and that in Ci and Ci/Mi groups were 3.37, 1.79 and 1.48 and 4.87, 1.88 and 1.67, for UM-UC-3, 5637 and Biu87 derived tumor, respectively (FIG. 5D). Elevated levels of both Ki67 and CD34 proteins indicate active cell proliferation and increased blood vasculature formation in the tumor mass. The percentage of Ki67-positive cells and the numbers of CD34 positive vascular structures in tumor xenografts were reduced by Ci, Ci/Mi and EH/Ci/Mi treatments relative to PBS controls (FIG. 5F-I). The highest reduction was with the tri-drug combination and the lowest with the single drugs, which is consistent with the effects on tumor growth of this tri-drug combination.

Comprehensive cancer genomic studies in the last few years have repeatedly demonstrated that genetic heterogeneity in cancer cells differentiates not only tumors from different individuals, but also different lesions, different part in a single lesion or different cancer cells in a cancer patient. This has been regarded as the major cause of failure in cancer treatment. Therefore, optimizing multi-drug regimen capable of killing a broad spectrum of cancer cells with different single drug-resistant profiles should be performed on a panel of established cancer cell lines to capture disease diversity in clinic. BCa consists of two major pathological subclasses, approximately 90% in the transitional cell carcinoma and 6% cases in the squamous cell carcinoma. In this study, seven TCC and one squamous carcinoma cell lines that vary dramatically in chemoresistance to five of six drug exposures (FIG. 2G) were used, intending to faithfully reflect the heterogeneous spectrum of BCa. This example used FSC platform, DF algorithm guided experimental testing (FIG. 1) to assess the cell killing capability of 100 out of 15625 possible combinations of a set of six drugs at five doses in four rounds of testing. A tri-drug regimen (EH/Ci/Mi, 1500 ng/mL Ci, 200 ng/mL Mi and 250 ng/mL EH) identified is able to kill 82.86% to 99.52% cancer cells of 7 TCC sand, 93.75% of 1 squamous BCa cell lines in comparison with 52.53% cells of the immortalized untransformed cells (Table S4). The ideal state of EH/Ci/M regime was confirmed from a statistic modeling analysis of the ACS readouts of 100 combinations tested.

This tri-drug regimen killed more BCa cells at 4 fold lower concentration than any of the component drug (Table S4), indicating a synergistic interaction among these three drugs when used together. This example has also shown that EH/Ci/Mi regimen was more potent than mono-drug and bi-drug combinations to inhibit the growth of tumor xenografts derived from 5637, UM-UC-3 and Biu87 cell lines in nude mice (FIG. 5). A further confirmation of its clinical utility awaits the forthcoming clinical investigation The current anti-bladder cancer combination chemotherapies are chiefly cisplatin-based: CMV (cisplatin, methotrexate, and vinblastine), M-VAC (methotrexate, vinblastine, adriamycin and cisplatin), and GC (gemcitabine plus cisplatin). Recent reports suggest a combined use of EH and Mi for BCa treatment. EH's mechanism of action is different from Ci and Mi that covalently bind DNA and repress both replication and transcription of DNA, leading to cell death. As an intercalating agent, EH affects the secondary structure of DNA and therefore inhibits transcription and induces apoptosis. Thus, use of these drugs at a lower dose together can simultaneously target different mechanisms for cancer cell killing along with a reduced level of cytotoxity of the normal cells as described in this study.

To understand why EH/Ci/Mi regimen is capable to kill a broad spectrum of BCa cells but each component drug event at three fold higher dose failed, this example analyzed the basal and drug-triggered activities of nine cancer associated signaling pathways in four bladder cancer cell lines (5637, UM-UC-3, Biu87 and H-bc) and a non-transformed bladder epithelial cell line (SV-HUC-1) (Table. S4): DNA damage response, Hypoxia, ER Stress, Heat Shock, Wnt, Notch, Cell cycling, Myc/Max and MAPK/ERK pathways (Table 4 and Table S5). Consistent with the chemoresistance of these cell lines, the basal level activities of these signaling pathways are collectively higher in chemoresistant cell lines (UM-UC-3, Biu87, H-bc and SV-HUC-1) than the most sensitive cell line, 5637 (FIG. 4 and Table S5). This example also found that the subsets of pathways activated by the tri-drug combination are similar to at least the set of pathways triggered by the dominant drug in all cell lines tested (Table 4 and Table S5). This observation offers a mechanistic explanation for why the EH/Ci/Mi can effectively kill all the cancer cell lines tested, but none of the four fold dosed component drugs failed.

By identifying EH/Ci/Mi regimen as a particular example for discovering effective BCa specific chemotherapeutic regimen, this example demonstrates both robustness and general applicability of the FSC platform to develop the effective drug (chemotherapeutics, biologicals and target therapeutics) combination therapy for cancer.

It should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The disclosures illustratively described herein may suitably be practiced in the absence of any element or elements, limitation or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

The invention claimed is:

1. A method for treating a human patient suffering from bladder cancer, comprising administering to the patient an effective amount of mitomycin, an effective amount of cisplatin and an effective amount of epirubicin, wherein the weight ratio of mitomycin to cisplatin to epirubicin is about 200 to 1500 to 250.

2. The method of claim 1, wherein the patient is not being treated with any of paclitaxel, docetaxel, fluorouracil (5-FU), methotrexate or vinblastine.

3. The method of claim 1, wherein the patient is not being treated with any other chemotherapeutic drug.

4. The method of claim 1, wherein the mitomycin is administered intravesically.

5. The method of claim 4, wherein the amount of mitomycin administered is from 20 mg to 60 mg in each treatment.

6. The method of claim 1, wherein the cisplatin is administered intravesically.

7. The method of claim 6, wherein the amount of cisplatin administered is from 50 mg to 150 mg in each treatment.

8. The method of claim 1, wherein the epirubicin is administered intravesically.

9. The method of claim 8, wherein the amount of epirubicin administered is from 5 mg to 200 mg in each treatment.

10. The method of claim 1, wherein at least one of the mitomycin, the cisplatin and the epirubicin is administered orally.

11. The method of claim 1, wherein the mitomycin, the cisplatin and the epirubicin are administered concurrently.

12. The method of claim 1, wherein the mitomycin, the cisplatin and the epirubicin are administered sequentially.

13. The method of claim 1, wherein the bladder cancer comprises transitional cell carcinoma.

* * * * *